(12) United States Patent
Tadaoka et al.

(10) Patent No.: US 10,293,215 B2
(45) Date of Patent: May 21, 2019

(54) RUBBER COMPOSITION, CROSSLINKED RUBBER MOLDED PRODUCT AND GOLF BALL

(71) Applicants: Dunlop Sports Co. Ltd., Kobe-shi, Hyogo (JP); Sumitomo Rubber Industries, Ltd., Kobe-shi, Hyogo (JP)

(72) Inventors: Hiroshi Tadaoka, Kobe (JP); Kazuyoshi Shiga, Kobe (JP)

(73) Assignee: SUMITOMO RUBBER INDUSTRIES, LTD., Kobe-shi, Hyogo (JP)

( * ) Notice: Subject to any disclaimer, the term of this patent is extended or adjusted under 35 U.S.C. 154(b) by 0 days.

(21) Appl. No.: 15/851,135

(22) Filed: Dec. 21, 2017

(65) Prior Publication Data
US 2018/0185706 A1    Jul. 5, 2018

(30) Foreign Application Priority Data

Dec. 22, 2016 (JP) ................................. 2016-250053
Dec. 22, 2016 (JP) ................................. 2016-250055
Dec. 22, 2016 (JP) ................................. 2016-250056
Jun. 30, 2017 (JP) ................................. 2017-129266
Jun. 30, 2017 (JP) ................................. 2017-129267

(51) Int. Cl.
| | |
|---|---|
| C08L 9/00 | (2006.01) |
| C08J 3/24 | (2006.01) |
| C08K 5/098 | (2006.01) |
| A63B 37/02 | (2006.01) |
| A63B 37/00 | (2006.01) |
| C08K 5/00 | (2006.01) |
| C07F 3/00 | (2006.01) |
| C08L 7/00 | (2006.01) |
| C07F 3/06 | (2006.01) |
| A63B 39/00 | (2006.01) |
| A63B 102/02 | (2015.01) |

(52) U.S. Cl.
CPC ............ *A63B 37/005* (2013.01); *C07F 3/003* (2013.01); *C07F 3/06* (2013.01); *C08J 3/24* (2013.01); *C08K 5/0025* (2013.01); *C08K 5/098* (2013.01); *C08L 7/00* (2013.01); *C08L 9/00* (2013.01); *A63B 37/0024* (2013.01); *A63B 37/0039* (2013.01); *A63B 37/0051* (2013.01); *A63B 2039/006* (2013.01); *A63B 2102/02* (2015.10); *A63B 2209/00* (2013.01)

(58) Field of Classification Search
None
See application file for complete search history.

(56) References Cited

U.S. PATENT DOCUMENTS

| | | | |
|---|---|---|---|
| 6,354,966 B1 | 3/2002 | Takemura et al. | |
| 2010/0151965 A1 | 6/2010 | Okamoto et al. | |
| 2018/0186816 A1* | 7/2018 | Tadaoka | ............... C07F 3/06 |

FOREIGN PATENT DOCUMENTS

| | | | |
|---|---|---|---|
| AU | B-29922/89 | * | 8/1989 |
| EP | 1 847 564 A1 | | 10/2007 |
| JP | 2001-087422 A | | 4/2001 |
| JP | 2001-161858 A | | 6/2001 |
| JP | 2004-292667 A | | 10/2004 |
| JP | 2006-241265 A | | 9/2006 |
| JP | 4062363 B1 | | 3/2008 |
| JP | 4811274 B2 | | 11/2011 |

* cited by examiner

*Primary Examiner* — David J Buttner
(74) *Attorney, Agent, or Firm* — Birch, Stewart, Kolasch & Birch, LLP

(57) ABSTRACT

An object of the present invention is to provide a rubber composition from which a crosslinked rubber molded product excellent in the resilience performance can be obtained. The present invention provides a rubber composition containing (a) a base rubber, (b) a co-crosslinking agent and (c) a crosslinking initiator, wherein (b) the co-crosslinking agent contains a complex represented by a general formula (1).

$$M_4OL_6 \quad (1)$$

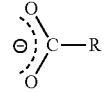

(2)

[In the formula (1), M is a metal atom, and L is a carboxylate represented by the general formula (2). In the formula (2), R is a hydrogen atom, an alkyl group having 1 to 18 carbon atoms, an alkenyl group having 2 to 18 carbon atoms or an alkynyl group having 2 to 18 carbon atoms, and the dotted line shows a resonance structure. In the formula (1), a plurality of R may be identical to or different from each other, and at least one of R is the alkenyl group having 2 to 18 carbon atoms or the alkynyl group having 2 to 18 carbon atoms.]

20 Claims, 5 Drawing Sheets

RUBBER COMPOSITION, CROSSLINKED RUBBER MOLDED PRODUCT AND GOLF BALL

FIELD OF THE INVENTION

The present invention relates to a rubber composition, more specifically, a rubber composition containing a novel co-crosslinking agent.

DESCRIPTION OF THE RELATED ART

Examples of the method for increasing a flight distance of a golf ball on driver shots include a method of utilizing a core having high resilience, and a method of utilizing a core having a hardness distribution in which the hardness increases from the core center towards the core surface. The former method has an effect of increasing the initial speed of the golf ball, and the latter method has an effect of increasing the launch angle and lowering the spin rate of the golf ball. A golf ball showing a high launch angle and a low spin rate travels a great flight distance.

Examples of the method of obtaining a core having high resilience include a method of forming a core with a multi-layer structure and controlling the property of each layer, and a method of forming a core from a rubber composition having high resilience. The method of controlling the property of each layer of the core, for example, is described in Japanese Patent Publications No. 2001-87422 A and 2001-161858 A. Japanese Patent Publication No. 2001-87422 A discloses a multi-piece solid golf ball wherein an inner core layer of the golf ball has an elastic modulus in a range from 50 to 200 MPa, and an outer core layer of the golf ball has a lower elastic modulus than the inner core layer only by 15 to 100 MPa (refer to paragraphs 0020, 0022). In addition, Japanese Patent Publication No. 2001-161858 A discloses a multi-piece solid golf ball wherein if an amount of an organic sulfur compound blended in an innermost core layer and an outermost core layer of the golf ball with respect to 100 parts by weight of a base rubber, is Hi and Ho, respectively, the formula 0≤Ho/Hi<1 is satisfied (refer to paragraph 0019).

As the method of forming a core from a rubber composition having high resilience, a technology of improving a base rubber blended in the rubber composition has been proposed. For example, Japanese Patent Publications No. 4062363 B and No. 2004-292667 A propose a rubber composition containing a high-cis polybutadiene as a base rubber, wherein the high-cis polybutadiene is synthesized by using a cobalt catalyst. Japanese Patent Publication No. 2006-241265 A proposes a rubber composition containing a high-cis polybutadiene (A) and a high-cis polybutadiene (B) in combination as a base rubber, wherein the high-cis polybutadiene (A) is synthesized by using a cobalt catalyst, and the high-cis polybutadiene (B) is synthesized by using a catalyst other than a cobalt catalyst (refer to paragraphs 0017, 0035). In addition, Japanese Patent Publications No. 4811274 B proposes a rubber composition containing a polybutadiene rubber (A) containing a syndiotactic polybutadiene, and a rubber other than (A) in combination as a base rubber (refer to paragraphs 0010, 0025).

SUMMARY OF THE INVENTION

Various rubber compositions for improving the resilience have been proposed. However, there is still room for improvement of the resilience performance. The present invention has been made in view of the above mentioned circumstances, and an object of the present invention is to provide a rubber composition providing a crosslinked rubber molded product excellent in the resilience performance.

The present invention that has solved the above problems provides a rubber composition containing (a) a base rubber, (b) a co-crosslinking agent and (c) a crosslinking initiator, wherein (b) the co-crosslinking agent contains a complex represented by a general formula (1).

[In the formula (1), M is a metal atom, and L is a carboxylate represented by the general formula (2). In the formula (2), R is a hydrogen atom, an alkyl group having 1 to 18 carbon atoms, an alkenyl group having 2 to 18 carbon atoms or an alkynyl group having 2 to 18 carbon atoms, and the dotted line shows a resonance structure. In the formula (1), a plurality of R may be identical to or different from each other, and at least one of R is the alkenyl group having 2 to 18 carbon atoms or the alkynyl group having 2 to 18 carbon atoms.]

The complex represented by the general formula (1) has a high affinity to (a) the base rubber, and thus has a high dispersibility in (a) the base rubber. Accordingly, the crosslinking point after the crosslinking has a small size (about 0.4 nm). In addition, the complex represented by the general formula (1) has formed a structure of a crosslinking point in advance. Accordingly, the crosslinking point can be formed merely by the reaction with the base rubber, and the crosslinking efficiency is high. Thus, if the rubber composition according to the present invention is used, a crosslinked rubber molded product excellent in the resilience performance can be obtained.

The present invention also includes a crosslinked rubber molded product formed from the above rubber composition. Further, the present invention also includes a golf ball comprising a constituent member formed from the above rubber composition.

If the rubber composition according to the present invention is used, a crosslinked rubber molded product excellent in the resilience performance can be obtained.

DESCRIPTION OF THE PREFERRED EMBODIMENT

[Rubber Composition]

Figure 1:
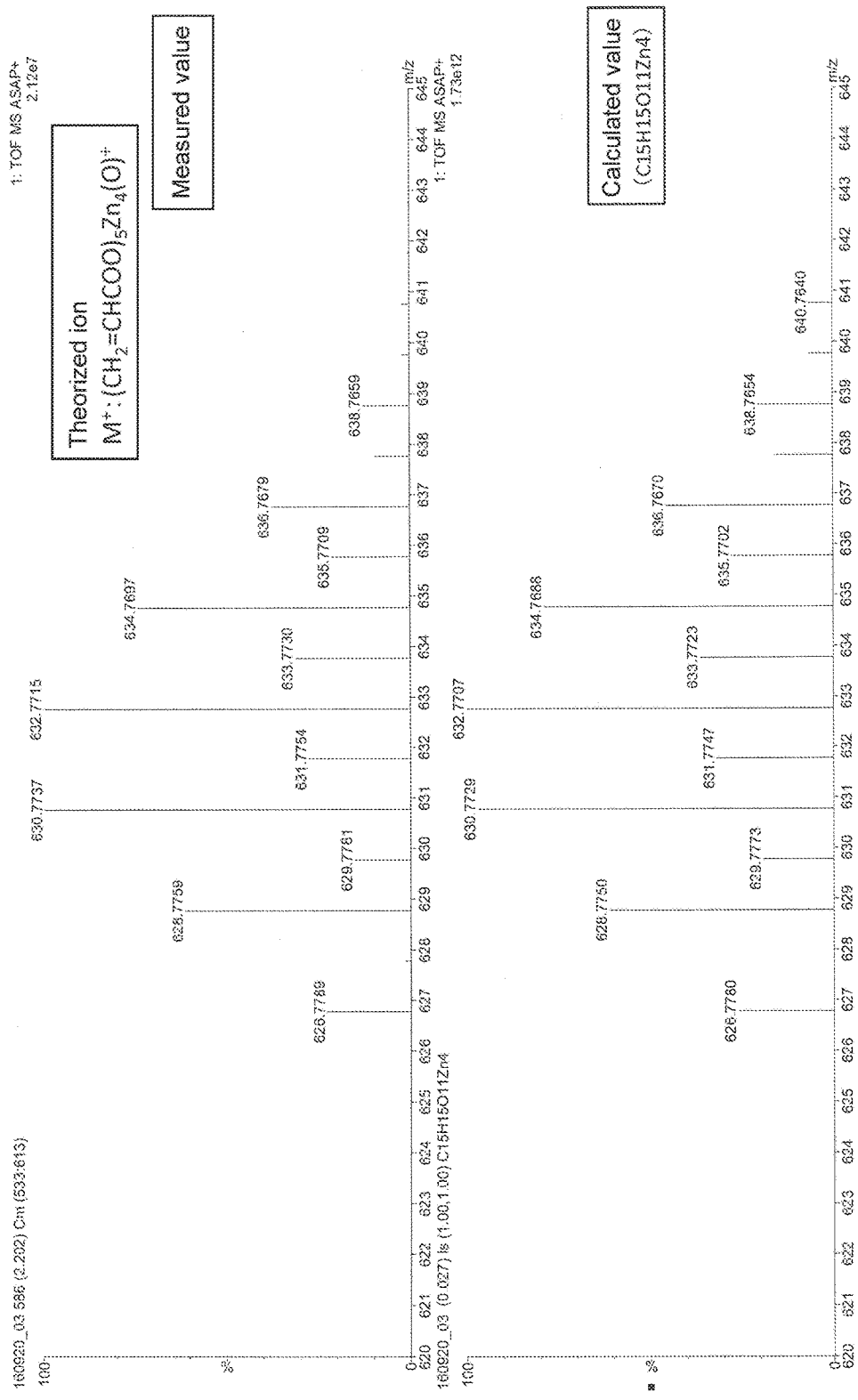
FIG. 1 shows ASAP-MS spectrum of acrylic acid oxo cluster.

The rubber composition according to the present invention contains (a) a base rubber, (b) a co-crosslinking agent and (c) a crosslinking initiator, wherein (b) the co-crosslinking agent contains a complex represented by a general formula (1) which will be described later.

A metal salt of an α,β-unsaturated carboxylic acid having 3 to 8 carbon atoms, which has been widely used as a co-crosslinking agent so far, is an ionic crystal, thus it has a low affinity to the base rubber and has a low dispersibility in the base rubber. In addition, such the metal salt of the α,β-unsaturated carboxylic acid forms crosslinking points by forming a graft chain by the oligomerization of the co-crosslinking agents and reacting with the base rubber. Accordingly, each crosslinking point has a great size (about 4 nm), and the crosslinking efficiency is low. On the contrary, the complex represented by the general formula (1) has a high affinity to (a) the base rubber, and thus has a high dispersibility in (a) the base rubber. Accordingly, the crosslinking point after the crosslinking has a small size (about 0.4 nm). In addition, the complex represented by the general formula (1) has formed a structure of a crosslinking point in advance. Accordingly, the crosslinking point can be formed merely by the reaction with the base rubber, and the crosslinking efficiency is high. Thus, if the rubber composition according to the present invention is used, a crosslinked rubber molded product excellent in the resilience performance can be obtained.

((a) Base Rubber)

As (a) the base rubber, a natural rubber and/or a synthetic rubber may be used. Examples of the synthetic rubber include a diene rubber such as polybutadiene rubber (BR), polyisoprene rubber (IR), styrene polybutadiene rubber (SBR), chloroprene rubber (CR), butyl rubber (IIR) and acrylonitrile butadiene rubber (NBR); and a non-diene rubber such as ethylene propylene rubber (EPM), ethylene-propylene-diene rubber (EPDM), urethane rubber, silicone rubber, acrylic rubber, epichlorohydrin rubber, polysulfide rubber, fluorine rubber and chlorosulfonated polyethylene rubber. These synthetic rubbers may be used solely, or at least two of them may be used in combination.

(a) The base rubber preferably contains the natural rubber and/or the diene rubber. The total amount of the natural rubber and/or the diene rubber in (a) the base rubber is preferably 50 mass % or more, more preferably 70 mass % or more, and even more preferably 90 mass % or more. It is also preferred that (a) the base rubber consists of the natural rubber and/or the diene rubber (a) The base rubber preferably contains the polybutadiene rubber. Particularly preferred is a high-cis polybutadiene having a cis-1,4-bond which is beneficial to the resilience in an amount of 40 mass % or more, preferably 80 mass % or more, and more preferably 90 mass % or more. The amount of the high-cis polybutadiene in (a) the base rubber is preferably 50 mass % or more, more preferably 70 mass % or more.

The high-cis polybutadiene preferably contains a 1,2-vinyl bond in an amount of 2.0 mass % or less, more preferably 1.7 mass % or less, and even more preferably 1.5 mass % or less. If the amount of the 1,2-vinyl bond is too large, the resilience may be lowered.

The high-cis polybutadiene preferably includes one synthesized using a rare-earth element catalyst. When a neodymium catalyst, which employs a neodymium compound of a lanthanum series rare-earth element compound, is used, a polybutadiene rubber having the cis-1,4 bond in a high amount and the 1,2-vinyl bond in a low amount is obtained with excellent polymerization activity. Such polybutadiene rubber is particularly preferred.

The high-cis polybutadiene preferably has a molecular weight distribution Mw/Mn (Mw: weight average molecular weight, Mn: number average molecular weight) of 2.0 or more, more preferably 2.2 or more, even more preferably 2.4 or more, and most preferably 2.6 or more, and preferably has a molecular weight distribution Mw/Mn of 6.0 or less, more preferably 5.0 or less, even more preferably 4.0 or less, and most preferably 3.4 or less. If the molecular weight distribution (Mw/Mn) of the high-cis polybutadiene is excessively low, the processability may deteriorate. If the molecular weight distribution (Mw/Mn) of the high-cis polybutadiene is excessively low, the workability may be lowered, and if the molecular weight distribution (Mw/Mn) of the high-cis polybutadiene is excessively high, the resilience may be lowered. It is noted that the measurement of the molecular weight distribution is conducted by gel permeation chromatography ("HLC-8120GPC" available from Tosoh Corporation) using a differential refractometer as a detector under the conditions of column: GMHHXL (available from Tosoh Corporation), column temperature: 40° C. and mobile phase: tetrahydrofuran, and calculated by converting based on polystyrene standard.

The high-cis polybutadiene preferably has a Mooney viscosity ($ML_{1+4}$ (100° C.)) of 30 or more, more preferably 32 or more, and even more preferably 35 or more, and preferably has a Mooney viscosity ($ML_{1+4}$ (100° C.)) of 140 or less, more preferably 120 or less, even more preferably 100 or less, and most preferably 80 or less. It is noted that the Mooney viscosity ($ML_{1+4}$ (100° C.)) in the present invention is a value measured according to JIS K6300 using an L rotor under the conditions of: a preheating time of 1 minute; a rotor rotation time of 4 minutes; and a temperature of 100° C.

((b) Co-Crosslinking Agent)

(b) The co-crosslinking agent contains a complex having a carboxylate as a ligand and represented by the general formula (1).

$$M_4OL_6 \tag{1}$$

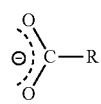

(2)

[In the formula (1), M is a metal atom, O is an oxygen atom, and L is a carboxylate represented by the general formula (2). In the formula (2), O is an oxygen atom, C is a carbon atom, R is a hydrogen atom, an alkyl group having 1 to 18 carbon atoms, an alkenyl group having 2 to 18 carbon atoms or an alkynyl group having 2 to 18 carbon atoms, and the dotted line shows a resonance structure. In the formula (1), a plurality of R may be identical to or different from each other, and at least one of R is the alkenyl group having 2 to 18 carbon atoms or the alkynyl group having 2 to 18 carbon atoms.]

Examples of the metal atom (M) include an alkali metal such as lithium, sodium, potassium, rubidium and cesium; an alkaline earth metal such as calcium, strontium and barium; a transition metal such as scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold; and a base metal such as beryllium, magnesium, aluminum, zinc, gallium, cadmium, indium, tin, thallium, lead, bismuth and polonium. These metal atoms may be used solely, or at least two of them may be used in combination. Among them, as the metal atom, the metal atom having oxidation number of +2 is preferable, and beryllium, magnesium, calcium, zinc, barium, cadmium or lead is more preferable. In the formula (1), a plurality of metal atoms (M) may be identical to or different from each other, and are preferably all identical to each other.

Examples of the alkyl group having 1 to 18 carbon atoms include methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, and octadecyl group. The alkyl group having 1 to 18 carbon atoms may have a linear structure, a branched structure or a cyclic structure, and the linear structure is preferable.

Examples of the alkenyl group having 2 to 18 carbon atoms include ethenyl group (vinyl group), 1-propenyl group, 2-propenyl group, isopropenyl group, 3-butenyl group, 4-pentenyl group, 5-hexenyl group, 6-heptenyl group, 7-octenyl group, 8-nonenyl group, 9-decenyl group, 10-undecenyl group, 11-dodecenyl group, 8-tridecenyl group, 12-tridecenyl group, 13-tetradecenyl group, 8-pentadecenyl group, 14-pentadecenyl group, 15-hexadecenyl group, 8-heptadecenyl group, 10-heptadecenyl group, 16-heptadecenyl group, and 17-octadecenyl group. The alkenyl group having 2 to 18 carbon atoms may have a linear structure or a branched structure, and the linear structure is preferable. As the alkenyl group having 2 to 18 carbon atoms, an alkenyl group having one carbon-carbon double bond is preferable, and an alkenyl group having a carbon-carbon double bond at a terminal thereof is more preferable. The alkenyl group preferably has 8 or less carbon atoms, more preferably 6 or less carbon atoms, and even more preferably 4 or less carbon atoms. Preferable examples of the alkenyl group having 2 to 18 carbon atoms include vinyl group, isopropenyl group, 1-propenyl group and 2-propenyl group.

Examples of the alkynyl group having 2 to 18 carbon atoms include ethynyl group, 1-propynyl group, 2-propynyl group, 3-butynyl group, 4-pentynyl group, 5-hexynyl group, 6-heptynyl group, 7-octynyl group, 8-nonynyl group, 9-decynyl group, 10-undecynyl group, 11-dodecynyl group, 8-tridecynyl group, 12-tridecynyl group, 13-tetradecynyl group, 8-pentadecynyl group, 14-pentadecynyl group, 15-hexadecynyl group, 8-heptadecynyl group, 10-heptadecynyl group, 16-heptadecynyl group, and 17-octadecynyl group. The alkynyl group having 2 to 18 carbon atoms may have a linear structure or a branched structure, and the linear structure is preferable. As the alkynyl group having 2 to 18 carbon atoms, an alkynyl group having one carbon-carbon triple bond is preferable, and an alkynyl group having a carbon-carbon triple bond at a terminal thereof is more preferable. The alkynyl group preferably has 8 or less carbon atoms, more preferably has 6 or less carbon atoms, and even more preferably has 4 or less carbon atoms. Preferable examples of the alkynyl group having 2 to 18 carbon atoms include ethynyl group, 1-propynyl group and 2-propynyl group.

In the formula (1), at least one of R is the alkenyl group having 2 to 18 carbon atoms or the alkynyl group having 2 to 18 carbon atoms. In other words, the complex represented by the formula (1) has one or more carbon-carbon unsaturated bonds. If the complex represented by the formula (1) has one or more carbon-carbon unsaturated bonds, the complex represented by the formula (1) is capable of reacting with (a) the base rubber. The number of the alkenyl group having 2 to 18 carbon atoms or alkynyl group having 2 to 18 carbon atoms in the above R is preferably 2 or more, more preferably 4 or more, even more preferably 5 or more, and most preferably 6. If the complex represented by the formula (1) has two or more carbon-carbon unsaturated bonds, the complex represented by the formula (1) is capable of crosslinking a plurality of molecular chains of (a) the base rubber.

In the formula (1), at least one of R is preferably an alkenyl group having 2 to 18 carbon atoms and a carbon-carbon double bond at a terminal thereof, or an alkynyl group having 2 to 18 carbon atoms and a carbon-carbon triple bond at a terminal thereof. The number of the alkenyl group having 2 to 18 carbon atoms and a carbon-carbon double bond at a terminal thereof or alkynyl group having 2 to 18 carbon atoms and having a carbon-carbon triple bond at a terminal thereof in the above R is preferably 2 or more, more preferably 4 or more, even more preferably 5 or more, and most preferably 6.

In the formula (1), six R may be identical to or different from each other, and are preferably all identical to each other.

Examples of the complex represented by the formula (1) include a complex (zinc acrylate oxo cluster) in which all the R are vinyl group and the metal atom (M) is zinc; and a complex (zinc methacrylate oxo cluster) in which all the R are isopropenyl group and the metal atom (M) is zinc.

Examples of the structure of the complex represented by the formula (1) include a structure having four metal atoms (M) bonding to an oxygen atom (O) and a carboxylate group (the formula (2)) coordinating to the metal atoms. Examples of the configuration of the four metal atoms bonding to the oxygen atom include a regular tetrahedron configuration and a planar quadrangle configuration. In addition, the coordination mode of the carboxylate group to the metal atoms is bidentate coordination. It is noted that the two oxygen atoms of the carboxylate group may coordinate to the different metal atom or to the same metal atom, and preferably coordinate to the different metal atom.

The complex represented by the general formula (1) is preferably a complex represented by a structural formula (3).

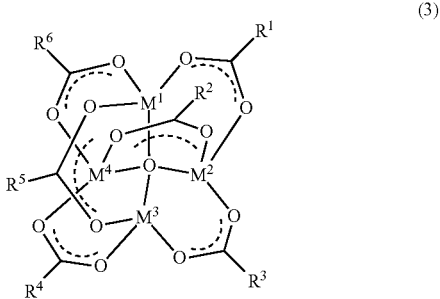

(3)

[In the formula (3), $M^1$ to $M^4$ are identical to or different from each other and represent a metal atom, O represents an oxygen atom, $R^1$ to $R^6$ are identical to or different from each other and represent a hydrogen atom, an alkyl group having 1 to 18 carbon atoms, an alkenyl group having 2 to 18 carbon atoms or an alkynyl group having 2 to 18 carbon atoms, and at least one of $R^1$ to $R^6$ is the alkenyl group having 2 to 18 carbon atoms or the alkynyl group having 2 to 18 carbon atoms.].

In the structural formula (3), the bond shown by the dotted line which is attached to the solid line is a hybrid bond of the carboxylate group. In addition, in the structural formula (3), the covalent bond and the coordination bond are both shown in a solid line.

Examples of the metal atoms represented by $M^1$ to $M^4$ in the formula (3) include those listed as M in the formula (1). Among them, as the metal atom, the metal atom having oxidation number of +2 is preferable, and beryllium, magnesium, calcium, zinc, barium, cadmium or lead is more preferable. The metal atoms represented by $M^1$ to $M^4$ may be different from each other, but are preferably all the same metal atom.

Examples of the alkyl group having 1 to 18 carbon atoms represented by $R^1$ to $R^6$ in the formula (3) include those listed as R in the formula (1). The alkyl group having 1 to 18 carbon atoms may have a linear structure, a branched structure or a cyclic structure, and the linear structure is preferable.

Examples of the alkenyl group having 2 to 18 carbon atoms represented by $R^1$ to $R^6$ in the formula (3) include those listed as R in the formula (1). The alkenyl group having 2 to 18 carbon atoms may have a linear structure or a branched structure, and the linear structure is preferable. As the alkenyl group having 2 to 18 carbon atoms, an alkenyl group having a carbon-carbon double bond at a terminal thereof is preferable. The alkenyl group preferably has 8 or less carbon atoms, more preferably 6 or less carbon atoms, and even more preferably 4 or less carbon atoms. Preferable examples of the alkenyl group having 2 to 18 carbon atoms include vinyl group, isopropenyl group, 1-propenyl group and 2-propenyl group.

Examples of the alkynyl group having 2 to 18 carbon atoms represented by $R^1$ to $R^6$ in the formula (3) include those listed as R in the formula (1). The alkynyl group having 2 to 18 carbon atoms may have a linear structure or a branched structure, and the linear structure is preferable. As the alkynyl group having 2 to 18 carbon atoms, an alkynyl group having a carbon-carbon triple bond at a terminal thereof is preferable, The alkynyl group preferably has 8 or less carbon atoms, more preferably 6 or less carbon atoms, and even more preferably 4 or less carbon atoms. Preferable examples of the alkynyl group having 2 to 18 carbon atoms include ethynyl group, 1-propynyl group and 2-propynyl group.

In the formula (3), at least one of $R^1$ to $R^6$ is the alkenyl group having 2 to 18 carbon atoms or the alkynyl group having 2 to 18 carbon atoms. The number of the alkenyl group having 2 to 18 carbon atoms or alkynyl group having 2 to 18 carbon atoms in the above $R^1$ to $R^6$ is preferably 2 or more, more preferably 4 or more, even more preferably 5 or more, and most preferably 6.

In the formula (3), at least one of $R^1$ to $R^6$ is preferably an alkenyl group having 2 to 18 carbon atoms and a carbon-carbon double bond at a terminal thereof, or an alkynyl group having 2 to 18 carbon atoms and a carbon-carbon triple bond at a terminal thereof. The number of the alkenyl group having 2 to 18 carbon atoms and a carbon-carbon double bond at a terminal thereof or alkynyl group having 2 to 18 carbon atoms and a carbon-carbon triple bond at a terminal thereof in the above $R^1$ to $R^6$ is preferably 2 or more, more preferably 4 or more, even more preferably 5 or more, and most preferably 6.

In the formula (3), $R^1$ to $R^6$ may be identical to or differentro each other, and are preferably all identical to each other.

In the formula (3), $R^1$ to $R^6$ are vinyl group or isopropenyl group, and the metal atom (M) is preferably a metal atom having oxidation number of +2, more preferably zinc.

(b) The co-crosslinking agent may further contain another co-crosslinking agent than the complex represented by the general formula (1), unless the other co-crosslinking agent impairs the effect of the present invention. Examples of the other co-crosslinking agent include an α,β-unsaturated carboxylic acid having 3 to 8 carbon atoms and/or a metal salt thereof. The α,β-unsaturated carboxylic acid having 3 to 8 carbon atoms and/or the metal salt thereof has an action of crosslinking a rubber molecule by graft polymerization to a base rubber molecular chain. Examples of the α,β-unsaturated carboxylic acid having 3 to 8 carbon atoms include acrylic acid, methacrylic acid, fumaric acid, maleic acid, and crotonic acid.

Examples of the metal constituting the metal salt of the α,β-unsaturated carboxylic acid having 3 to 8 carbon atoms include a monovalent metal ion such as sodium, potassium and lithium; a divalent metal ion such as magnesium, calcium, zinc, barium and cadmium; a trivalent metal ion such as aluminum; and other metal ion such as tin and zirconium. The metal component may be used solely or as a mixture of at least two of them, Among them, as the metal component, the divalent metal such as magnesium, calcium, zinc, barium, cadmium or the like is preferred. This is because use of the divalent metal salt of the α,β-unsaturated carboxylic acid having 3 to 8 carbon atoms easily generates a metal crosslinking between the rubber molecules.

In the case that the other co-crosslinking agent is used, the amount of the complex represented by the general formula (1) in (b) the co-crosslinking agent is preferably 5 mass % or more, more preferably 20 mass % or more, even more preferably 50 mass % or more, and most preferably 80 mass % or more. It is noted that it is also preferred that (b) the co-crosslinking agent of the rubber composition consists of the complex represented by the general formula (1).

The amount of (b) the co-crosslinking agent in the core composition is preferably 1 part by mass or more, more preferably 3 parts by mass or more, and even more preferably 5 parts by mass or more, and is preferably 50 parts by mass or less, more preferably 45 parts by mass or less, and even more preferably 40 parts by mass or less, with respect to 100 parts by mass of (a) the base rubber. If the amount of (b) the co-crosslinking agent is less than 1 part by mass, the amount of (c) the crosslinking initiator which will be described later must be increased in order to obtain an appropriate hardness of the constituent member formed from the rubber composition, which tends to lower the resilience of the molded product of the crosslinked rubber. On the other hand, if the amount of (b) the co-crosslinking agent exceeds 50 parts by mass, the constituent member formed from the rubber composition tends to become too hard.

((c) Crosslinking Initiator)

(c) The crosslinking initiator is blended in order to cross ink (a) the base rubber component. As (c) the crosslinking initiator, an organic peroxide is preferred. Examples of the organic peroxide include peroxy ketal, dialkyl peroxide, diacyl peroxide, and peroxy ester. Examples of the peroxy ketal include 1,1-di(t-hexylperoxy) cyclohexane, 1,1-di(t-butylperoxy) cyclohexane, n-butyl-4,4-di-(t-butylperoxy valerate), and 1,1-bis(t-butylperoxy)-3,3,5-trimethyl cyclohexane. Examples of the dialkyl peroxide include dicumyl peroxide, di(2-t-butylperoxyisopropyl) benzene, t-butylcumyl peroxide, 2,5-dimethyl-2,5-di(t-butylperoxy) hexane, 2,5-dimethyl-2,5-di(t-butylperoxy) hexyne-3, and di-t-butyl peroxide. Examples of the peroxy ester include 2,5-dimethyl-2,5-di(benzoylperoxy) hexane, t-hexylperoxy benzoate, and t-butylperoxy benzoate. These organic peroxides may be used solely, or at least two of them may be used in combination. Among them, dicumyl peroxide is preferably used.

The amount of (c) the crosslinking initiator is preferably 0.2 part by mass or more, more preferably 0.5 part by mass or more, and even more preferably 0.7 part by mass or more, and is preferably 50 parts by mass or less, more preferably 45 parts by mass or less, even more preferably 40 parts by mass or less, and most preferably 35 parts by mass or less, with respect to 100 parts by mass of (a) the base rubber. If the amount of (c) the crosslinking initiator is less than 0.2 part by mass, the constituent member formed from the rubber composition becomes so soft that the resilience of the crosslinked rubber molded product may be lowered, and if the amount of (c) the crosslinking initiator exceeds 50 parts by mass, the amount of (b) the co-crosslinking agent which has been described above must be decreased in order to obtain an appropriate hardness of the constituent member formed from the rubber composition, which may lower the resilience of the crosslinked rubber molded product or worsen the durability of the crosslinked rubber molded product.

((d) Metal Compound)

The rubber composition may further contain (d) a metal compound. Examples of (d) the metal compound includes a metal hydroxide such as magnesium hydroxide, zinc hydroxide, calcium hydroxide, sodium hydroxide, lithium hydroxide, potassium hydroxide and copper hydroxide; a metal oxide such as magnesium oxide, calcium oxide, zinc oxide and copper oxide; and a metal carbonate such as magnesium carbonate, zinc carbonate, calcium carbonate, sodium carbonate, lithium carbonate and potassium carbonate. (d) The metal compound may be used solely or as a mixture of at least two of them. As (d) the metal compound, the metal oxide is preferable, at least one member selected from the group consisting of magnesium oxide, calcium oxide and zinc oxide is more preferable.

The amount of (d) the metal compound in the rubber composition is preferably 0.5 part by mass or more, more preferably 1 part by mass or more, and even more preferably 1.5 parts by mass or more, and is preferably 20 parts by mass or less, more preferably 15 parts by mass or less, and even more preferably 10 parts by mass or less, with respect to 100 parts by mass of (a) the base rubber, ((e) Carboxylic Acid and/or Salt Thereof)

The rubber composition may further contain (e) a carboxylic acid and/or a salt thereof. If (e) the carboxylic acid and/or the salt thereof is contained, the hardness distribution of the obtained crosslinked rubber molded product can be controlled. Examples of (e) the carboxylic acid and/or the salt thereof include an aliphatic carboxylic acid, an aliphatic carboxylic acid salt, an aromatic carboxylic acid, and an aromatic carboxylic acid salt. (e) The carboxylic acid and/or the salt may be used solely or as a mixture of at least two of them. It is noted that (e) the carboxylic acid and/or the salt thereof excludes the complex represented by the general formula (1) and the α,β-unsaturated carboxylic acid having 3 to 8 carbon atoms and/or the metal salt thereof which are used as (b) the co-crosslinking agent.

The aliphatic carboxylic acid may be a saturated aliphatic carboxylic acid (hereinafter, sometimes referred to as "saturated fatty acid"), or an unsaturated aliphatic carboxylic acid (hereinafter, sometimes referred to as "unsaturated fatty acid"). Further, the aliphatic carboxylic acid may have a branched structure or a cyclic structure. The saturated fatty acid preferably has 6 or more and 24 or less carbon atoms, more preferably 18 or less carbon atoms, and even more preferably 13 or less carbon atoms. The unsaturated fatty acid preferably has 6 or more carbon atoms, more preferably 7 or more carbon atoms, and even more preferably 8 or more carbon atoms, and preferably has 24 or less carbon atoms, more preferably 18 or less carbon atoms, and even more preferably 13 or less carbon atoms.

Examples of the aromatic carboxylic acid include a carboxylic acid having a benzene ring in the molecule, and a carboxylic acid having an aromatic heterocycle in the molecule. The aromatic carboxylic acid may be used solely or as a mixture of at least two of them. Examples of the carboxylic acid having a benzene ring include an aromatic carboxylic acid having a carboxyl group directly bonding to a benzene ring, an aromatic-aliphatic carboxylic acid having an aliphatic carboxylic acid bonding to a benzene ring, a polynuclear aromatic carboxylic acid having a carboxyl group directly bonding to a fused benzene ring, and a polynuclear aromatic-aliphatic carboxylic acid having an aliphatic carboxylic acid bonding to a fused benzene ring. Examples of the carboxylic acid having an aromatic heterocycle include a carboxylic acid having a carboxyl group directly bonding to an aromatic heterocycle.

As the aliphatic carboxylic acid salt or aromatic carboxylic acid salt, a salt of the above-mentioned aliphatic carboxylic acid or aromatic carboxylic acid can be used. Examples of the cation component of the salt include a metal ion, an ammonium ion, and an organic cation. The cation component may be used solely or as a mixture of at least two of them. Examples of the metal ion include a monovalent metal ion such as sodium, potassium, lithium and silver; a divalent metal ion such as magnesium, calcium, zinc, barium, cadmium, copper, cobalt, nickel and manganese; a trivalent metal ion such as aluminum and iron; and other metal ion such as tin, zirconium and titanium. Among them, the metal ion is preferably the divalent metal ion, and more preferably magnesium, zinc or calcium.

The organic cation is a cation having a carbon chain. The organic cation is not particularly limited, and examples thereof include an organic ammonium ion. Examples of the organic ammonium ion include a primary ammonium ion such as stearyl ammonium ion, hexyl ammonium ion, octyl ammonium ion and 2-ethylhexyl ammonium ion; a secondary ammonium ion such as dodecyl(aury) ammonium ion and octadecyl(stearyl) ammonium ion; a tertiary ammonium ion such as trioctyl ammonium ion; and a quaternary ammonium ion such as dioctyldimethyl ammonium ion and distearyldimethyl ammonium ion. These organic cations may be used solely or as a mixture of at least two of them.

Examples of the aliphatic carboxylic acid and/or the salt thereof include a saturated fatty acid and/or a salt thereof, and an unsaturated fatty acid and/or a salt thereof. The saturated fatty acid and/or the salt thereof is preferred, caprylic acid (octanoic acid), pelargonic acid (nonanoic acid), capric acid (decanoic acid), lauric acid, myristic acid, palmitic acid, stearic acid, behenic acid, and/or potassium salt, magnesium salt, calcium salt, aluminum salt, zinc salt, iron salt, copper salt, nickel salt, cobalt salt of these saturated fatty acids are more preferred. Preferable examples of the unsaturated fatty acid and/or the salt thereof include palmitoleic acid, oleic acid, linoleic acid, arachidonic acid, and/or potassium salt, magnesium salt, calcium salt, aluminum salt, zinc salt, iron salt, copper salt, nickel salt, cobalt salt of these unsaturated fatty acids.

Preferable examples of the aromatic carboxylic acid and/or the salt thereof include benzoic acid, butylbenzoic acid, anisic acid (methoxybenzoic acid), dimethoxybenzoic acid, trimethoxybenzoic acid, dimethylaminobenzoic acid, chlorobenzoic acid, dichlorobenzoic acid, trichlorobenzoic acid, acetoxybenzoic acid, biphenylcarboxylic acid, naphthalenecarboxylic acid, anthracenecarboxylic acid, furancarboxylic acid, thenoic acid, and/or potassium salt, magnesium salt, calcium salt, aluminum salt, zinc salt, iron salt, copper salt, nickel salt, cobalt salt of these aromatic carboxylic acids.

The amount of (e) the carboxylic acid and/or the salt thereof, for example, is preferably 1 part by mass or more, more preferably 2 parts by mass or more, and even more preferably 3 parts by mass or more, and is preferably 30 parts by mass or less, more preferably 20 parts by mass or less, and even more preferably 15 parts by mass or less, with respect to 100 parts by mass of (a) the base rubber.

((f) Organic Sulfur Compound)

The rubber composition may further contain (f) an organic sulfur compound. Examples of (f) the organic sulfur compound include at least one compound selected from the group consisting of thiophenols, thionaphthols, polysulfides, thiurams, thiocarboxylic acids, dithiocarboxylic acids, sulfenamides, dithiocarbamates, thiazoles, and metal salts thereof. (f) The organic sulfur compound is preferably an organic sulfur compound having a thiol group (—SH) or a metal salt thereof, and more preferably thiophenols, thionaphthols or metal salts thereof.

Examples of the thiols include thiophenols and thionaphthols. Examples of the thiophenols include thiophenol; thiophenols substituted with a fluoro group, such as 4-fluorothiophenol, 2,5-difluorothiophenol, 2,6-difluorothiophenol, 2,4,5-trifluorothiophenol, 2,4,5,6-tetrafluorothiophenol and pentafluorothiophenol; thiophenols substituted with a chloro group, such as 2-chlorothiophenol, 4-chlorothiophenol, 2,4-dichlorothiophenol, 2,5-dichlorothiophenol, 2,6-dichlorothiophenol, 2,4,5-trichlorothiophenol, 2,4,5,6-tetrachlorothiophenol and pentachlorothiophenol; thiophenols substituted with a bromo group, such as 4-bromothiophenol, 2,5-dibromothiophenol, 2,6-dibromothiophenol, 2,4,5-tribromothiophenol, 2,4,5,6-tetrabromothiophenol and pentabromothiophenol; thiophenols substituted with an iodo group, such as 4-iodothiophenol, 2,5-diiodothiophenol, 2,6-diiodothiophenol, 2,4,5-triiodothiophenol, 2,4,5,6-tetraiodothiophenol and pentaiodothiophenol; and metal salts thereof. As the metal salt, a zinc salt is preferred.

Examples of the thionaphthols (naphthalenethiols) include 2-thionaphthol, 1-thionaphthol, 1-chloro-2-thionaphthol, 2-chloro-1-thionaphthol, 1-bromo-2-thionaphthol, 2-bromo-1-thionaphthol, 1-fluoro-2-thionaphthol, 2-fluoro-1-thionaphthol, 1-cyano-2-thionaphthol, 2-cyano-1-thionaphthol, 1-acetyl-2-thionaphthol, 2-acetyl-1-thionaphthol, and metal salts thereof. Among them, 2-thionaphthol, 1-thionaphthol, and metal salts thereof are preferable. The metal salt is preferably a divalent metal salt, more preferably a zinc salt. Specific examples of the metal salt include zinc salt of 1-thionaphthol and zinc salt of 2-thionaphthol.

The polysulfides are organic sulfur compounds having a polysulfide bond, and examples thereof include disulfides, trisulfides and tetrasulfides. The polysulfides are preferably diphenyl polysulfides.

Examples of the diphenyl polysulfides include diphenyl disulfide; diphenyl disulfides substituted with a halogen group, such as bis(4-fluorophenyl)disulfide, bis(2,5-difluorophenyl)disulfide, bis(2,6-difluorophenyl)disulfide, bis(2,4,5-trifluorophenyl)disulfide, bis(2,4,5,6-tetrafluorophenyl)disulfide, bis(pentafluorophenyl)disulfide, bis(4-chlorophenyl)disulfide, bis(2,5-dichlorophenyl)disulfide, bis(2,6-dichlorophenyl)disulfide, bis(2,4,5-trichlorophenyl)disulfide, bis(2,4,5,6-tetrachlorophenyl)disulfide, bis(pentachlorophenyl)disulfide, bis(4-bromophenyl)disulfide, bis(2,5-dibromophenyl)disulfide, bis(2,6-dibromophenyl)disulfide, bis(2,4,5-tribromophenyl)disulfide, bis(2,4,5,6-tetrabromophenyl)disulfide, bis(pentabromophenyl)disulfide, bis(4-iodophenyl)disulfide, bis(2,5-diiodophenyl)disulfide, bis(2,6-diiodophenyl)disulfide, bis(2,4,5-triiodophenyl)disulfide, bis(2,4,5,6-tetraiodophenyl)disulfide, and bis(pentaiodophenyl)disulfide; and diphenyl disulfides substituted with an alkyl group, such as bis(4-methylphenyl)disulfide, bis(2,4,5-trimethylphenyl)disulfide, bis(pentamethylphenyOdisulfide, bis(4-t-butylphenyl)disulfide, bis(2,4,5-tri-t-butylphenyl)disulfide, and bis(penta-t-butylphenyl)disulfide.

Examples of the thiurams include thiuram monosulfides such as tetramethylthiuram monosulfide; thiuram disulfides such as tetramethylthiuram disulfide, tetraethylthiuram disulfide and tetrabutylthiuram disulfide; and thiuram tetrasulfides such as dipentamethylenethiuram tetrasulfide. Examples of the thiocarboxylic acids include a naphthalene thiocarboxylic acid. Examples of the dithiocarboxylic acids include a naphthalene dithiocarboxylic acid. Examples of the sulfenamides include N-cyclohexyl-2-benzothiazole sulfenamide, N-oxydiethylene-2-benzothiazole sulfenamide, and N-t-butyl-2-benzothiazole sulfenamide.

(f) The organic sulfur compound may be used solely, or at least two of them may be used in combination. (f) The organic sulfur compound is preferably the thiophenols and/or the metal salts thereof, the thionaphthols and/or the metal salts thereof, the diphenyl disulfides and the thiuram disulfides, and more preferably 2,4-dichlorothiophenol, 2,6-difluorothiophenol, 2,6-dichlorothiophenol, 2,6-dibromothiophenol, 2,6-diiodothiophenol, 2,4,5-trichlorothiophenol, pentachlorothiophenol, 1-thionaphthol, 2-thionaphthol, diphenyl disulfide, bis(2,6-difluorophenyl)disulfide, bis(2,6-dichlorophenyl)disulfide, bis(2,6-dibromophenyl)disulfide, bis(2,6-diiodophenyl)disulfide and bis(pentabromophenyl)disulfide.

The amount of (f) the organic sulfur compound is preferably 0.05 part by mass or more, more preferably 0.1 part by mass or more, and is preferably 5.0 parts by mass or less, more preferably 2.0 parts by mass or less, with respect to 100 parts by mass of (a) the base rubber. If the amount of (f) the organic sulfur compound is less than 0.05 part by mass, the effect of adding (f) the organic sulfur compound is not obtained, and thus the resilience of the golf ball may not improve. In addition, if the amount of (f) the organic sulfur compound exceeds 5.0 parts by mass, the obtained golf ball has so great compression deformation amount that the resilience thereof may be lowered.

(Other Component)

The rubber composition may further contain additives such as a pigment, a filler for adjusting weight, an antioxidant, a peptizing agent and a softener, where necessary. In addition, the rubber composition may contain a rubber powder which is obtained by pulverizing a golf ball core or offcuts produced when preparing a core.

Examples of the pigment blended in the rubber composition include a white pigment, a blue pigment, and a purple pigment. As the white pigment, titanium oxide is preferably used. The type of titanium oxide is not particularly limited, but rutile type is preferably used because of the high opacity thereof. In addition, the amount of titanium oxide is preferably 0.5 part by mass or more, more preferably 2 parts by mass or more, and is preferably 8 parts by mass or less, more preferably 5 parts by mass or less, with respect to 100 parts by mass of (a) the base rubber.

It is also preferred that the rubber composition contains both a white pigment and a blue pigment. The blue pigment is blended in order to cause white color to be vivid, and examples thereof include ultramarine blue, cobalt blue, and phthalocyanine blue. In addition, examples of the purple pigment include anthraquinone violet, dioxazine violet, and methyl violet.

The filler blended in the rubber composition is mainly used as a weight adjusting agent for adjusting the weight of the crosslinked rubber molded product, and may be blended where necessary. Examples of the filler include an inorganic filler such as zinc oxide, barium sulfate, calcium carbonate, magnesium oxide, tungsten powder, and molybdenum powder. The amount of the filler is preferably 0.5 part by mass or more, more preferably 1 part by mass or more, and is preferably 30 parts by mass or less, more preferably 25 parts by mass or less, and even more preferably 20 parts by mass or less, with respect to 100 parts by mass of (a) the base rubber. This is because if the amount of the filler is less than 0.5 part by mass, the weight adjusting tends to become difficult, and if the amount of the filler exceeds 30 parts by mass, the weight proportion of the rubber component becomes low and thus the resilience tends to be lowered.

The amount of the antioxidant is preferably 0.1 part by mass or more and 1 part by mass or less with respect to 100 parts by mass of (a) the base rubber. In addition, the amount of the peptizing agent is preferably 0.1 part by mass or more and 5 parts by mass or less with respect to 100 parts by mass of (a) the base rubber.

[Process of Preparing the Rubber Composition]
(Preparation of the Complex Represented by the General Formula (1))

The complex represented by the general formula (1) can be obtained by contacting a fatty acid metal salt and a metal oxide. Examples of the process of preparing the complex represented by the general formula (1) include a preparing process comprising: a step of dissolving or dispersing the fatty acid metal salt and the metal oxide in a first solvent and stirring the resultant reaction liquid (reaction step); a step of removing an insoluble substance from the reaction liquid (insoluble substance removal step); and a step of removing the solvent from the reaction liquid (drying step).

(Reaction Step)

In the reaction step, the fatty acid metal salt and the metal oxide are dissolved or dispersed in a first solvent, and the resultant reaction liquid is stirred. In this step, the fatty acid metal salt and the metal oxide are contacted in the solvent to produce the complex represented by the general formula (1).

The fatty acid metal salt is not particularly limited, as long as it is capable of forming the ligand represented by the general formula (2). The fatty acid metal salt may be used solely, or at least two of them may be used in combination.

Examples of the fatty acid constituting the fatty acid metal salt include a saturated fatty acid having 1 to 19 carbon atoms, and an unsaturated fatty acid having 3 to 20 carbon atoms. Examples of the saturated fatty acid include methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, and nonadecanoic acid. Examples of the unsaturated fatty acid include an unsaturated fatty acid having a carbon-carbon double bond such as propenoic acid (acrylic acid), 2-methylprop-2-enoic acid (methacrylic acid), 2-butenoic acid, 3-butenoic acid, 4-pentenoic acid, 5-hexenoic acid, 6-heptenoic acid, 7-octenoic acid, 8-nonenoic acid, 9-decenoic acid, 10-undecenoic acid, 11-dodecenoic acid, 12-tridecenoic acid, 9-tetradecenoic acid, 13-tetradecenoic acid, 14-pentadecenoic acid, 9-hexadecenoic acid, 15-hexadecenoic acid, 16-heptadecenoic acid, 9-octadecenoic acid, 11-octadecenoic acid, 17-octadecenoic acid and 18-nonadecenoic acid; and an unsaturated fatty acid having a carbon-carbon triple bond such as propiolic acid, 3-butynoic acid, 4-pentynoic acid, 5-hexynoic acid, 6-heptynoic acid, 7-octynoic acid, 8-nonynoic acid, 9-decynoic acid, 10-undecynoic acid, 11-dodecynoic acid, 12-tridecynoic acid, 9-tetradecynoic acid, 13-tetradecynoic acid, 14-pentadecynoic acid, 9-hexadecynoic acid, 15-hexadecynoic acid, 16-heptadecynoic acid, 9-octadecynoic acid, 11-octadecynoic acid, 17-octadecynoic acid, and 18-nonadecynoic acid.

The unsaturated fatty acid having a carbon-carbon double bond is preferably a fatty acid having one carbon-carbon double bond, and more preferably a fatty acid having a carbon-carbon double bond at a terminal thereof. The unsaturated fatty acid having a carbon-carbon triple bond is preferably a fatty acid having one carbon-carbon triple bond, and more preferably a fatty acid having a carbon-carbon triple bond at a terminal thereof.

Examples of the metal atom constituting the fatty acid metal salt include an alkali metal such as lithium, sodium, potassium, rubidium and cesium; an alkaline earth metal such as calcium, strontium and barium; a transition metal such as scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold; a base metal such as beryllium, magnesium, aluminum, zinc, gallium, cadmium, indium, tin, thallium, lead, bismuth and polonium. Among them, as the metal atom, the metal atom capable of forming a divalent metal ion is preferable, and beryllium, magnesium, calcium, zinc, barium, cadmium or lead is more preferable. These metal ions may be used solely, or a mixture of at least two of them may be used.

The fatty acid metal salt is preferably a fatty acid metal salt in which the metal ion is a divalent metal ion, more preferably an unsaturated fatty acid metal salt in which the metal ion is a divalent metal ion, even more preferably an acrylic acid or methacrylic acid metal salt in which the metal ion is a divalent metal ion, and most preferably zinc acrylate or zinc methacrylate.

When two or more of the fatty acid metal salts are used in combination, the amount of each fatty acid metal salt can be suitably adjusted in accordance with the desirable complex. The amount of the unsaturated fatty acid in the fatty acid constituting the fatty acid metal salt is preferably 33 mol % or more, more preferably 50 mol % or more, and even more preferably 66 mol % or more. It is also preferable that all the fatty acids constituting the fatty acid metal salt are the unsaturated fatty acid. In addition, the amount of the unsaturated fatty acid having a carbon-carbon double bond in the fatty acid constituting the fatty acid metal salt is preferably 33 mol % or more, more preferably 50 mol % or more, and even more preferably 66 mol % or more. It is also preferable that all the fatty acids constituting the fatty acid metal salt are the unsaturated fatty acid having a carbon-carbon double bond. As the fatty acid constituting the fatty acid metal salt, a plurality of fatty acids may be used in combination, but one fatty acid is preferably used.

Examples of the embodiment of the fatty acid metal salt include an embodiment including one fatty acid and one metal ion; an embodiment including a plurality of fatty acids and one metal ion; an embodiment including one fatty acid and a plurality of metal ions; and an embodiment including a plurality of fatty acids and a plurality of metal ions. Among them, the embodiment including one fatty acid and one metal ion is preferable.

Examples of the metal oxide include an alkali metal oxide such as lithium oxide, sodium oxide, potassium oxide, rubidium oxide and cesium oxide; an alkaline earth metal oxide such as calcium oxide, strontium oxide and barium oxide; a transition metal oxide such as scandium oxide, titanium oxide, vanadium oxide, chromium oxide, manganese oxide, iron oxide, cobalt oxide, nickel oxide, copper oxide, yttrium oxide, zirconium oxide, niobium oxide, molybdenum oxide, technetium oxide, ruthenium oxide, rhodium oxide, palladium oxide, silver oxide, hafnium oxide, tantalum oxide, tungsten oxide, rhenium oxide, osmium oxide, iridium oxide, platinum oxide and gold oxide; and a base metal oxide such as beryllium oxide, magnesium oxide, aluminum oxide, zinc oxide, gallium oxide, cadmium oxide, indium oxide, tin oxide, thallium oxide, lead oxide, bismuth oxide and polonium oxide. These metal oxides may be used solely, or a mixture of at least two of them may be used. Among them, as the metal oxide, the divalent metal oxide is preferable, and beryllium oxide, magnesium oxide, calcium oxide, zinc oxide, barium oxide, cadmium oxide or lead oxide is more preferable.

The combination of the fatty acid metal salt with the metal oxide is preferably, but is not limited to, a combination in which the metal constituting the fatty acid metal salt is identical to the metal constituting the metal oxide. The combination of the fatty acid metal salt with the metal oxide is preferably a combination of a fatty acid zinc salt with zinc oxide, more preferably a combination of an unsaturated fatty acid zinc salt with zinc oxide, and even more preferably a combination of zinc acrylate and/or zinc methacrylate with zinc oxide.

The first solvent is a solvent capable of dissolving the complex represented by the general formula (1) generated by the reaction. Examples of the first solvent include dichloromethane, 1,2-dichloroethane and chloroform.

In the reaction liquid, the mixing ratio (molar ratio) (fatty acid/metal oxide) of the fatty acid in the fatty acid metal salt to the metal oxide is preferably 1.0 or more, more preferably 1.5 or more, and even more preferably 2.0 or more, and is preferably 6.0 or less, more preferably 5.0 or less, and even more preferably 4.0 or less. If the mixing ratio falls within the above range, the desired complex can be produced in a good yield.

The amount of the solvent is preferably 1000 parts by mass or more, more preferably 2000 parts by mass or more, and even more preferably 3000 parts by mass or more, and is preferably 10000 parts by mass or less, more preferably 8000 parts by mass or less, and even more preferably 6000 parts by mass or less, with respect to 100 parts by mass of a total amount of the fatty acid metal salt and the metal oxide. If the amount of the solvent is 1000 parts by mass or more, the yield of the complex is higher, and if the amount of the solvent is 10000 parts by mass or less, the synthetic workload can be lowered.

The liquid temperature when stirring the reaction liquid is preferably 0° C. or more, more preferably 10° C. or more, and even more preferably 20° C. or more, and is preferably 100° C. or less, more preferably 90° C. or less, and even more preferably 80° C. or less. If the liquid temperature is 0° C. or more, the reaction speed is greater and the yield of the complex is higher, and if the liquid temperature is 100° C. or less, the reaction of unsaturated bonds of the carboxylate is suppressed and thus the yield of the complex is higher.

The time of stirring the reaction liquid is preferably 1 hour or more, more preferably 3 hours or more, and even more preferably 12 hours or more, and is preferably 300 hours or less, more preferably 200 hours or less, and even more preferably 100 hours or less.

(Insoluble Substance Removal Step)

In the insoluble substance removal step, the insoluble substance is removed from the reaction liquid after the reaction. The insoluble substance is considered to be the unreacted metal oxide or fatty acid metal salt remained in the solvent. In addition, if the liquid temperature when performing the reaction is high, it is considered that a polymer of the unsaturated fatty acid metal salt is also generated as the insoluble substance.

Examples of the method of removing the insoluble substance from the reaction liquid after the reaction include a method of filtering the reaction liquid.

(Drying Step)

In the drying step, the solvent is removed from the reaction liquid from which the insoluble substance has been removed. A mixture containing the complex represented by the general formula (1) and the fatty acid metal salt is obtained by removing the solvent.

Examples of the method of removing the solvent include a method of drying under reduced pressure and a method of drying under heating, and the drying under reduced pressure is preferable. When performing the drying under reduced pressure, the reaction liquid may be heated. The temperature of the reaction liquid when performing the drying is preferably 100° C. or less, more preferably 80° C. or less, and even more preferably 60° C. or less.

The preparing process may further comprise a step of purifying the complex represented by the general formula (1). It is noted that when the step of purifying the complex is comprised, the above-mentioned insoluble substance removal step may be omitted. Examples of the purification method include a method of removing the fatty acid metal salt from the reaction liquid in the preparing process (a method including a purification step): and a method of performing reprecipitation of the mixture of the complex represented by the general formula (1) and the fatty acid metal salt obtained in the preparing process (a method including a reprecipitation step). Among them, the method of removing the fatty acid metal salt from the reaction liquid in the preparing process is preferable, (Purification Step)

In the purification step, a second solvent is charged into the reaction liquid from which the insoluble substance has been removed in the preparing process, and the resultant precipitate is removed. Impurities such as the fatty acid metal salt are precipitated by charging the second solvent into the reaction liquid. The purity of the finally obtained complex represented by the general formula (1) can be enhanced by removing the precipitate.

The second solvent is not particularly limited, as long as it can selectively precipitate the fatty acid metal salt in the reaction liquid. In other words, the solubility of the complex represented by the general formula (1) in the second solvent is higher than the solubility of the fatty acid metal salt in the second solvent. Examples of the second solvent include hydrocarbons such as hexane, pentane, cyclohexane and heptane.

The amount of the second solvent may be suitably adjusted such that the fatty acid metal salt can be precipitated. The amount of the second solvent is preferably 10 parts by mass or more, more preferably 20 parts by mass or more, and even more preferably 30 parts by mass or more, and is preferably 200 parts by mass or less, more preferably 150 parts by mass or less, and even more preferably 100 parts by mass or less, with respect to 100 parts by mass of the amount of the first solvent.

In addition, after the second solvent is charged, a part of the first solvent and second solvent may be removed to precipitate the fatty acid metal salt. As the method of removing a part of the first solvent and second solvent, drying under reduced pressure is preferable. When performing the drying under reduced pressure, the reaction liquid may be heated. The temperature of drying the reaction liquid is preferably 100° C. or less, more preferably 80° C. or less, and even more preferably 60° C. or less.

Examples of the method of removing the precipitated fatty acid metal salt include a method of filtering the reaction liquid. The complex represented by the general formula (1) is obtained by removing the first solvent and the second solvent from the reaction liquid from which the precipitate has been removed, in the drying step. It is noted that the purification step may be performed several times depending on the desired purity of the complex represented by the general formula (1).

(Reprecipitation Step)

In the reprecipitation step, the reprecipitation of the mixture of the complex represented by the general formula (1) and the fatty acid metal salt obtained in the preparing process is performed. Specifically, the mixture of the complex represented by the general formula (1) and the fatty acid metal salt obtained in the preparing process is dissolved in the first solvent, the second solvent is charged into the resultant solution to precipitate the fatty acid metal salt, and the precipitate is removed.

As the first solvent and the second solvent used in the reprecipitation step, those listed in the reaction step and the purification step may be used. In addition, the preferable amount of the second solvent and the preferable method of removing the precipitate are identical to those in the purification step. The complex represented by the general formula (1) is obtained by removing the solvent after the precipitate is removed. The preferable method of removing the solvent is identical to that in the drying step. It is noted that the reprecipitation step may be performed several times depending on the desired purity of the complex represented by the general formula (1).

[Preparation of Rubber Composition]

The above rubber composition can be obtained by mixing and kneading (a) the base rubber, (b) the co-crosslinking agent, (c) the crosslinking initiator, and where necessary, (d) the metal compound, (e) the carboxylic acid and/or the salt thereof, (f) the organic sulfur compound and the other additives. The kneading can be conducted, without any limitation, for example, with a conventional kneading machine such as a kneading roll, a banbury mixer and a kneader.

[Crosslinked Rubber Molded Product]

The crosslinked rubber molded product according to the present invention is formed from the above rubber composition. The crosslinked rubber molded product can be formed by molding the kneaded rubber composition in a mold. The molding temperature is preferably 120° C. or more, more preferably 150° C. or more, and is preferably 250° C. or less. In addition, the pressure when performing the molding preferably ranges from 2.9 MPa to 11.8 MPa. The molding time preferably ranges from 10 minutes to 60 minutes.

The slab hardness of the crosslinked rubber molded product is preferably 20 or more, more preferably 25 or more, and even more preferably 30 or more, and is preferably 98 or less, more preferably 96 or less, and even more preferably 95 or less in Shore C hardness. If the slab hardness is 20 or more in Shore C hardness, the crosslinked structure is sufficiently formed and thus the crosslinked rubber molded product has enhanced durability, and if the slab hardness is 98 or less in Shore C hardness, the crosslinked rubber molded product has further enhanced resilience.

The Lupke type rebound resilience of the crosslinked rubber molded product is preferably 55% or more, more preferably 60% or more, and even more preferably 65% or more, and is preferably 98% or less, more preferably 95% or less, and even more preferably 90% or less. If the Lupke type rebound resilience is 55% or more, the crosslinked rubber molded product has further enhanced resilience, and if the Lupke type rebound resilience is 98% or less, the crosslinked rubber molded product is sufficiently hard and thus the durability thereof is enhanced.

The storage modulus E' (Pa) of the crosslinked rubber molded product is preferably $3.0 \times 10^7$ Pa or more, more preferably $5.0 \times 10^7$ Pa or more, and even more preferably $10 \times 10^7$ Pa or more, and is preferably $40 \times 10^7$ Pa or less, more preferably $35 \times 10^7$ Pa or less, and even more preferably $30 \times 10^7$ Pa or less. If the storage modulus E' (Pa) is $3.0 \times 10^7$ Pa or more, the crosslinked rubber molded product has further enhanced resilience, and if the storage modulus E' (Pa) is $40 \times 10^7$ Pa or less, the crosslinked rubber molded product has suitable hardness.

The loss modulus E" (Pa) of the crosslinked rubber molded product is preferably $0.001 \times 10^7$ Pa or more, more preferably $0.005 \times 10^7$ Pa or more, and even more preferably $0.01 \times 10^7$ Pa or more, and is preferably $3.0 \times 10^7$ Pa or less, more preferably $1.0 \times 10^7$ Pa or less, and even more preferably $0.5 \times 10^7$ Pa or less. If the loss modulus E" (Pa) is $0.001 \times 10^7$ Pa or more, the crosslinked structure is sufficiently formed and thus the crosslinked rubber molded product has enhanced durability, and if the loss modulus E" (Pa) is $3.0 \times 10^7$ Pa or less, the crosslinked rubber molded product has suitable viscosity and thus the resilience thereof is enhanced.

The slab hardness (Shore C) X and the Lupke type rebound resilience (%) Y of the above crosslinked rubber molded product formed from the rubber composition preferably satisfy a relationship of $Y \geq 87 - 0.283X$. The crosslinked rubber molded product satisfying the above relationship is excellent in the resilience performance.

The slab hardness (Shore C) X and the Lupke type rebound resilience (%) Y of the crosslinked rubber molded product preferably satisfy a relationship of $Y \geq 88 - 0.283X$, and more preferably satisfies a relationship of $Y \geq 89 - 0.283X$.

The storage modulus E' (Pa) and the loss modulus E" (Pa), which are measured with a dynamic viscoelasticity measuring apparatus (tensile mode), and the slab hardness (Shore C) X of the crosslinked rubber molded product formed from the above rubber composition preferably satisfy a relationship of $|\log(E'/E''^2)|/X \times 100 \leq 5.7$. The crosslinked rubber molded product satisfying the above relationship has a great hardness and is excellent in the resilience performance.

The storage modulus E' (Pa), the loss modulus E" (Pa) and the slab hardness (Shore C) X of the crosslinked rubber molded product preferably satisfy a relationship of $|\log(E'/E''^2)|/X \times 100 \leq 5.6$, and more preferably satisfy a relationship of $|\log(E'/E''^2)|/X \times 100 \leq 5.5$.

Examples of the application of the crosslinked rubber molded product include sports goods such as golf ball, tennis ball and grip, industrial products such as hose, belt and mat, shoe sole, tire, resin additive, antivibration rubber, and fender. Examples of the golf ball include a golf ball comprising a constituent member formed from the above rubber composition.

EXAMPLES

Next, the present invention will be described in detail by way of examples. However, the present invention is not limited to the examples described below. Various changes and modifications without departing from the spirit of the present invention are included in the scope of the present invention.

[Evaluation Method]
(1) Direct Introduction-Mass Analysis (DI-MS)

The mass analysis was carried out with a mass analyzer (SynaptG2-S type available from Waters Corporation).

Ionization method: atmospheric solids analysis probe (ASAP)

Measuring mode: Pos., Neg.

Measuring range: m/z=50 to 1500

(2) CHN Element Analysis

The element analysis was carried out with an organic trace element analyzer (Micro Corder JM10 type available from J-Science Lab Co., Ltd.).

(3) Zinc Amount Measurement

The zinc acrylate oxo cluster (0.1171 g) was weighed and put into a beaker with a volume of 100 ml, and 50 ml of distilled water was added to dissolve the complex. Into the resultant liquid, 10 ml of acetic acid-sodium acetate (pH 5) buffer was added, and some drops of a XO indicator (0.1 w/v % of xylenol orange solution for titration available from Wako Pure Chemical Industries, Ltd.: 0.1 g/100 ml=0.001396 M) were added. Finally, distilled water was added to adjust the liquid volume to 100 ml. The obtained liquid was titrated with 0.05 mol/l of an EDTA standard titrant (available from Dojin Chemical, Inc.).

(4) Infrared Spectroscopic Analysis

The infrared spectroscopic analysis was carried out with a Fourier transform infrared spectrophotometer ("Spectrum One" available from PerkinElmer, Inc.) by a total reflection absorption measuring method (ATR method) using diamond as a prism of the total reflection absorption measurement.

(5) Powder X-Ray Diffraction

The X-ray diffraction measurement was carried out with a wide angle X-ray diffraction instrument ("RINT-TTR III type" available from Rigaku Corporation). The measuring sample was pulverized with an agate mortar. The measuring conditions were as follows.

X-ray source: CuKα X-ray

Tube voltage-tube current: 50 kV-300 mA

Step width: 0.02 deg.

Measuring speed: 5 deg./min

Slit system: light diffusion-light reception-light scattering: 0.5 deg.-opening-0.5 deg.

Monochromator: diffraction curve bent-crystal monochromator (6) Slab Hardness (Shore C Hardness)

Sheets with a thickness of about 2 mm were prepared by heat molding the rubber composition, and stored at 23° C. for two weeks. It is noted that the heat molding was conducted according to the temperature and time shown in Tables 1, 2. At least three of these sheets were stacked on one another so as not to be affected by the measuring substrate on which the sheets were placed, and the hardness of the stack was measured with an automatic hardness tester (Digitest II, available from Bareiss company) using a detector of "Shore C".

(7) Lupke Type Rebound Resilience

The rebound resilience test was carried out according to JIS K6255 (2013). Sheets with a thickness of about 2 mm were prepared by heat molding the rubber composition, It is noted that the heat molding was conducted according to the temperature and time shown in Tables 1, 2. A cylindrical test piece with a thickness of about 12 mm and a diameter of 28 mm was prepared by punching the sheet obtained above into a circular shape with a diameter of 28 mm, and stacking six of the obtained circular sheets. The test piece was stored at a temperature of 23° C. plus or minus 2° C. and a relative humidity of 50% plus or minus 5% for 12 hours. The rebound resilience of the obtained test piece was measured with a Lupke type rebound resilience tester (available from Ueshima Seisakusho Co., Ltd.). The planar part of the stacked test pieces obtained above was held by a mechanical fixing method during the measurement, and the measurement was carried out at a temperature of 23° C., relative humidity of 50%, impact end diameter of 12.50 mm plus or minus 0.05 mm, impact mass of 0.35 kg plus or minus 0.01 kg and impact speed of 1.4 m/s plus or minus 0.01 m/s, (8) Measurement of Storage Modulus E' (Pa) and Loss Modulus E" (Pa)

The storage modulus E' (Pa) and the loss modulus E" (Pa) of the crosslinked rubber molded product were measured under the following conditions.

Apparatus: Dynamic viscoelasticity measuring apparatus "Rheogel-E4000" available from UBM Co., Ltd.

Test piece: A sheet with a thickness of 0.5 mm was prepared by press molding the rubber composition under the conditions shown in Tables 5, 6, and a test piece was cut from the sheet to have a width of 4 mm and a length between clamps of 20 mm, Measuring mode: tensile mode Measuring temp.: 24° C.

Oscillation frequency: 10 Hz

Measuring strain: 0.05%

[Production of Zinc Acrylate Oxo Cluster]

Zinc oxide (0.125 kg, 1.54 mol) and zinc acrylate (0.955 kg, 4.60 mol) were added in 24.9 kg of dichloromethane, and stirred at 40° C. for 48 hours. It is noted that the solvent was refluxed. 48 hours later, the reaction liquid was filtered to remove the precipitate. 9.83 kg of hexane was added in the filtrate, and concentration under reduced pressure was performed until the liquid amount was reduced to about one-fourth. The concentrate was filtered, and the filtrate was concentrated and dried to obtain zinc acrylate oxo cluster (615 g, yield 57 mass %).

The mass analysis, element analysis, zinc amount measurement, X-ray diffraction measurement and infrared spectroscopic analysis were conducted for the above obtained zinc acrylate oxo cluster. The experimental results are each shown below.

High-resolution ASAP-MS (positive) spectrum measurement results

Positive ion HR-ASAP-MS m/z; 632.7715
$[M-CH_2CHCOO]^+$ (calcd. For $C_{15}H_{15}O_{11}Zn_4$ 632.7707 $\Delta$1.2 ppm High-resolution ASAP-MS (negative) spectrum measurement results Negative ion HR-ASAP-MS m/z: 735.7762
$[M+O_2]^-$ (calcd. For $C_{18}H_{18}O_{15}Zn_4$ 735.7740 $\Delta$2.9 ppm
Anal. Calcd for $C_{18}H_{18}O_{13}Zn_4$: C, 30.71; H, 2.58. Found: C, 30.72; H, 2.50.

IR spectrum peak: 520 $cm^{-1}$, 600 $cm^{-1}$, 675 $cm^{-1}$, 828 $cm^{-1}$, 968 $cm^{-1}$, 1067 $cm^{-1}$, 1276 $cm^{-1}$, 1370 $cm^{-1}$, 1436 $cm^{-1}$, 1572 $cm^{-1}$, 1643 $cm^{-1}$.

Figure 2:
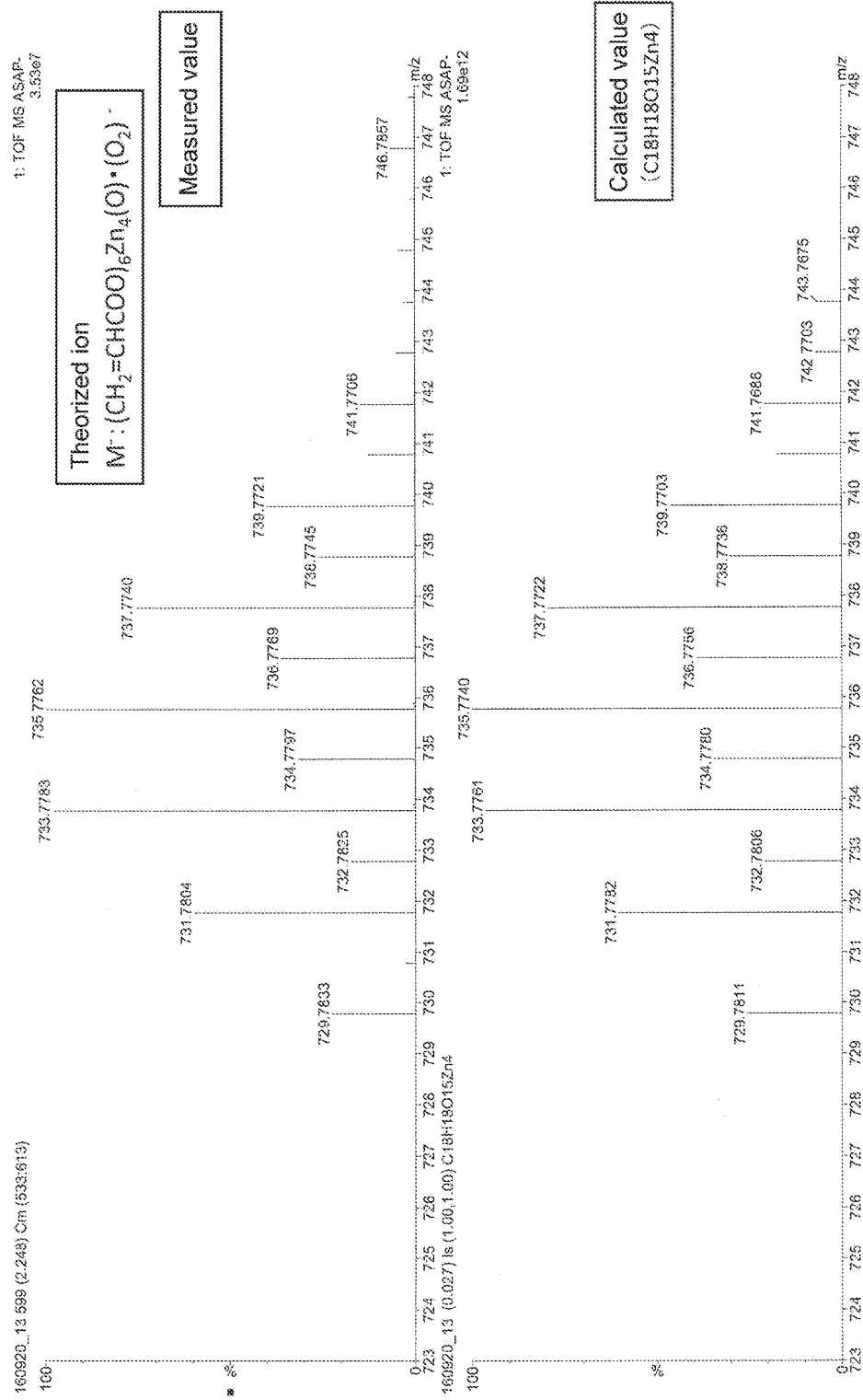
FIG. 2 shows ASAP-MS spectrum of acrylic acid oxo cluster.

ASAP-MS spectra of the zinc acrylate oxo cluster are shown in FIGS. 1, 2. In addition, ASAP-MS spectrum simulation patterns of anion $[Zn_4O(OCOCHCH_3)_6O_2]^{(-)}$ and cation $[Zn_4O(OCOCHCH_3)_5]^{(+)}$ theorized from $Zn_4O(OCOCHCH_2)_6$ are shown in FIGS. 1, 2. As shown in FIGS. 1, 2, the ASAP-MS spectrum has the same pattern as the simulation pattern. Further, the obtained experimental values 632.7715 and 735.7762 are very close to the estimated values which is 632.7707 for the cation $[Zn_4O(OCOCHCH_3)_5]^{(+)}$: $C_{15}H_{15}O_{11}Zn_4$ and 735.7740 for the anion $[Zn_4O(OCOCHCH_3)_6O_2]^{(-)}$: $C_{18}H_{18}O_{15}Zn_4$. In addition, the measured value of the zinc amount is 36.8 mass % which is very close to the theoretical value 37.2 mass %. Based on these results, it can be confirmed that the above prepared zinc acrylate oxo cluster is the compound represented by $Zn_4O(OCOCHCH_2)_6$.

The element analysis results show that the zinc acrylate oxo cluster contains carbon in an amount of 30.72 mass % and hydrogen in an amount of 2.50 mass %. The differences between the analysis results and the estimated values were 0.01 mass % for the carbon amount and 0.08 mass % for the hydrogen amount. Since the atomic compositions are very close to the estimated values, it can be confirmed that the zinc acrylate oxo cluster ($Zn_4O(OCOCHCH_2)_6$) has a very high purity.

Figure 3:
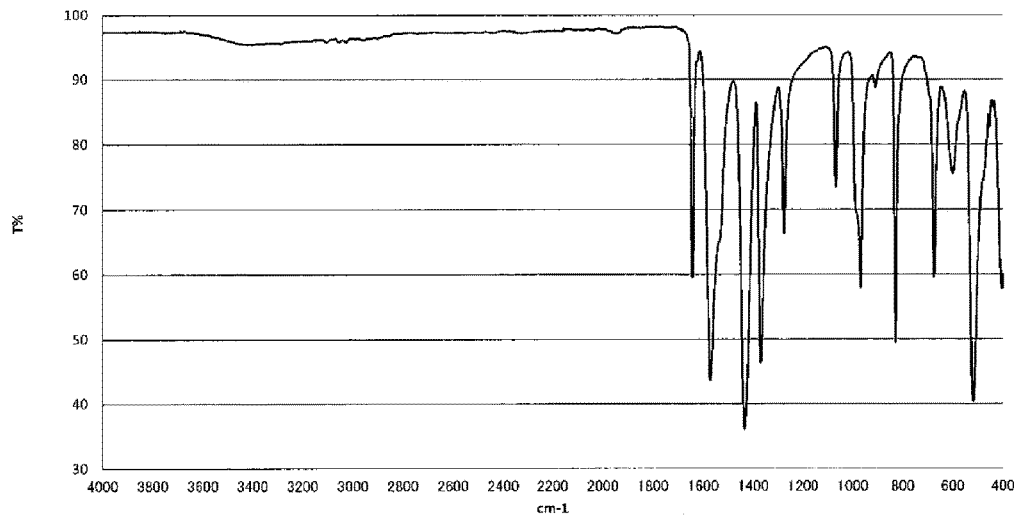
FIG. 3 shows IR spectrum of acrylic acid oxo cluster.
Figure 4:
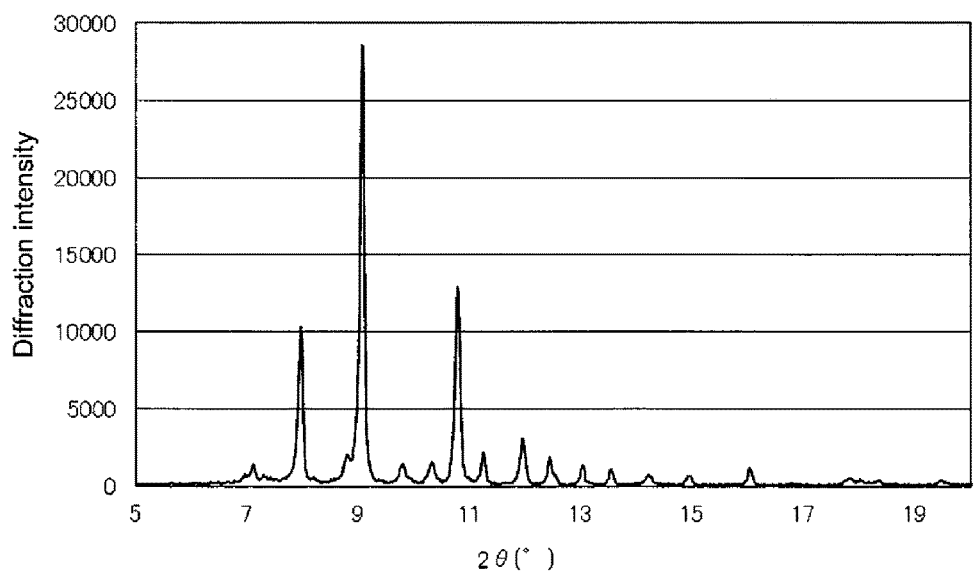
FIG. 4 shows X-ray diffraction spectrum of acrylic acid oxo cluster.

FIG. 3 shows IR spectrum, and FIG. 4 shows X-ray diffraction spectrum. Based on the IR spectrum, the absorption attributed to the vinyl group of acrylate and the absorption attributed to the vibration of $Zn_4O$ are confirmed. Further, it is also confirmed that the carboxylate group has a different coordination state from zinc diacrylate. Based on the X-ray diffraction spectrum, it is confirmed that the zinc acrylate oxo cluster has a different crystal structure from zinc diacrylate.

[Preparation of Rubber Composition]

Materials having the formulations shown in Tables 1-6 were kneaded to prepare rubber compositions. It is noted that the material temperature at the time of kneading the rubber compositions was set as 60° C. to 125° C.

TABLE 1

| | | Rubber composition No. | 1 | 2 | 3 | 4 | 5 | 6 | 7 | 8 | 9 | 10 |
|---|---|---|---|---|---|---|---|---|---|---|---|---|
| Formulation (parts by mass) | (a) | BR730 | 100 | 100 | 100 | 100 | 100 | 100 | 100 | 100 | 100 | 100 |
| | (b) | Zinc acrylate oxo cluster | 20 | 20 | 30 | 30 | 40 | 40 | 35 | 30 | 25 | 20 |
| | | ZNDA90S | — | — | — | — | — | — | 5 | 10 | 15 | 20 |
| | (d) | Zinc oxide | 2.69 | 2.69 | 2.69 | 2.69 | 2.69 | 2.69 | 3.2 | 3.7 | 4.3 | 4.8 |
| | (c) | Dicumyl peroxide | 0.8 | 0.8 | 0.8 | 0.8 | 0.8 | 0.8 | 0.8 | 0.8 | 0.8 | 0.8 |
| Crosslinking component | | Acrylate (parts by mass) | 12.1 | 12.1 | 18.2 | 18.2 | 24.2 | 24.2 | 24.3 | 24.3 | 24.4 | 24.4 |
| | | Zinc (parts by mass) | 9.6 | 9.6 | 13.3 | 13.3 | 17.0 | 17.0 | 17.0 | 17.0 | 17.0 | 17.0 |
| Evaluation | Molding conditions | Temperature (° C.) | 150 | 170 | 150 | 170 | 150 | 170 | 150 | 150 | 150 | 150 |
| | | Time (min) | 20 | 20 | 20 | 20 | 20 | 20 | 20 | 20 | 20 | 20 |
| | Slab properties | Shore C hardness | 58.3 | 60.6 | 68.0 | 70.8 | 77.6 | 80.9 | 82.1 | 83.3 | 84.4 | 85.6 |
| | | Lupke type rebound resilience (%) | 76.2 | 75.0 | 76.6 | 75.2 | 72.9 | 71.3 | 70.2 | 69.1 | 68.0 | 66.9 |

TABLE 2

| | | Rubber composition No. | 11 | 12 | 13 | 14 | 15 | 16 |
|---|---|---|---|---|---|---|---|---|
| Formulation (parts by mass) | (a) | BR730 | 100 | 100 | 100 | 100 | 100 | 100 |
| | (b) | ZNDA90S | 19.7 | 19.7 | 29.6 | 29.6 | 39.4 | 39.4 |
| | (d) | Zinc oxide | 5 | 5 | 5 | 5 | 5 | 5 |
| | (c) | Dicumyl peroxide | 0.8 | 0.8 | 0.8 | 0.8 | 0.8 | 0.8 |
| Crosslinking component | | Acrylate (parts by mass) | 12.1 | 12.1 | 18.2 | 18.2 | 24.3 | 24.3 |
| | | Zinc (parts by mass) | 9.6 | 9.6 | 12.4 | 12.4 | 15.2 | 15.2 |
| Evaluation | Molding conditions | Temperature (° C.) | 150 | 170 | 150 | 170 | 150 | 170 |
| | | Time (min) | 20 | 20 | 20 | 20 | 20 | 20 |
| | Slab properties | Shore C hardness | 58.9 | 62.6 | 75.5 | 79.2 | 85.0 | 89.1 |
| | | Lupke type rebound resilience (%) | 69.5 | 67.2 | 65.4 | 63.8 | 61.7 | 60.0 |

TABLE 3

| | | Rubber composition No. | 21 | 22 | 23 | 24 | 25 | 26 | 27 | 28 | 29 | 30 |
|---|---|---|---|---|---|---|---|---|---|---|---|---|
| Formulation (parts by mass) | (a) | BR730 | 100 | 100 | 100 | 100 | 100 | 100 | 100 | 100 | 100 | 100 |
| | (b) | Zinc acrylate oxo cluster | 20.5 | 20.5 | 31 | 31 | 41 | 41 | 35 | 30 | 25 | 20 |
| | | ZNDA90S | | | | | | | 5 | 10 | 15 | 20 |
| | (d) | Zinc oxide | 2.69 | 2.69 | 2.69 | 2.69 | 2.69 | 2.69 | 3.2 | 3.7 | 4.3 | 4.8 |
| | (c) | Dicumyl peroxide | 0.8 | 0.8 | 0.8 | 0.8 | 0.8 | 0.8 | 0.8 | 0.8 | 0.8 | 0.8 |

TABLE 3-continued

| | | Rubber composition No. | 21 | 22 | 23 | 24 | 25 | 26 | 27 | 28 | 29 | 30 |
|---|---|---|---|---|---|---|---|---|---|---|---|---|
| Crosslinking component | | Acrylate (parts by mass) | 12.1 | 12.1 | 18.3 | 18.3 | 24.2 | 24.2 | 23.8 | 23.9 | 24.0 | 24.1 |
| | | Zinc (parts by mass) | 9.6 | 9.6 | 13.4 | 13.4 | 17.0 | 17.0 | 16.7 | 16.7 | 16.8 | 16.8 |
| Evaluation | Molding conditions | Temperature (° C.) | 150 | 170 | 150 | 170 | 150 | 170 | 150 | 150 | 150 | 150 |
| | | Time (min) | 20 | 20 | 20 | 20 | 20 | 20 | 20 | 20 | 20 | 20 |
| | Properties | Slab hardness (Shore C) | 58.3 | 60.6 | 68.0 | 70.8 | 77.6 | 80.9 | 82.1 | 83.3 | 84.4 | 85.6 |
| | | Lupke type rebound resilience (%) | 76.2 | 75.0 | 76.6 | 75.2 | 72.9 | 71.3 | 70.2 | 69.1 | 68.0 | 66.9 |
| | | Rebound resilience/slab hardness | 1.31 | 1.24 | 1.13 | 1.06 | 0.94 | 0.88 | 0.855 | 0.830 | 0.805 | 0.782 |

TABLE 4

| | | Rubber composition No. | 31 | 32 | 33 | 34 | 35 | 36 |
|---|---|---|---|---|---|---|---|---|
| Formulation (parts by mass) | (a) | BR730 | 100 | 100 | 100 | 100 | 100 | 100 |
| | (b) | ZNDA90S | 19.65 | 19.65 | 29.55 | 29.55 | 39.4 | 39.4 |
| | (d) | Zinc oxide | 5 | 5 | 5 | 5 | 5 | 5 |
| | (c) | Dicumyl peroxide | 0.8 | 0.8 | 0.8 | 0.8 | 0.8 | 0.8 |
| Crosslinking component | | Acrylate (parts by mass) | 12.1 | 12.1 | 18.2 | 18.2 | 24.3 | 24.3 |
| | | Zinc (parts by mass) | 9.6 | 9.6 | 12.4 | 12.4 | 15.2 | 15.2 |
| Evaluation | Molding conditions | Temperature (° C.) | 150 | 170 | 150 | 170 | 150 | 170 |
| | | Time (min) | 20 | 20 | 20 | 20 | 20 | 20 |
| | Properties | Slab hardness (Shore C) | 58.9 | 62.6 | 75.5 | 79.2 | 85.0 | 89.1 |
| | | Lupke type rebound resilience (%) | 69.5 | 67.2 | 65.4 | 63.8 | 61.7 | 60.0 |
| | | Rebound resilience/slab hardness | 1.18 | 1.07 | 0.87 | 0.81 | 0.73 | 0.67 |

TABLE 5

| | | Rubber composition No. | 41 | 42 | 43 | 44 | 45 | 46 |
|---|---|---|---|---|---|---|---|---|
| Formulation (parts by mass) | (a) | BR730 | 100 | 100 | 100 | 100 | 100 | 100 |
| | (b) | Zinc acrylate oxo cluster | 31 | 41 | 35 | 30 | 25 | 20 |
| | | ZNDA90S | — | — | 5 | 10 | 15 | 20 |
| | (d) | Zinc oxide | 2.69 | 2.69 | 3.2 | 3.7 | 4.3 | 4.8 |
| | (c) | Dicumyl peroxide | 0.8 | 0.8 | 0.8 | 0.8 | 0.8 | 0.8 |
| Crosslinking component | | Acrylate (parts by mass) | 18.3 | 24.2 | 23.8 | 23.9 | 24.0 | 24.1 |
| | | Zinc (parts by mass) | 13.4 | 17.0 | 16.7 | 16.7 | 16.8 | 16.8 |
| Evaluation | Molding conditions | Temperature (° C.) | 170 | 170 | 150 | 150 | 150 | 150 |
| | | Time (min) | 20 | 20 | 20 | 20 | 20 | 20 |
| | Slab properties | Shore C hardness | 70.8 | 80.9 | 82.1 | 83.3 | 84.4 | 85.6 |
| | | Lupke type rebound resilience (%) | 75.2 | 71.3 | 70.2 | 69.1 | 68.0 | 66.9 |
| | | Storage modulus E' ($\times 10^7$ Pa) | 6.8 | 13.4 | 12.8 | 13.9 | 16.6 | 15.5 |
| | | Loss modulus E'' ($\times 10^7$ Pa) | 0.089 | 0.16 | 0.19 | 0.21 | 0.20 | 0.26 |
| | | $|\log(E'/E''^2)|$ | 4.0 | 4.3 | 4.5 | 4.5 | 4.4 | 4.6 |
| | | $|\log(E'/E''^2)/\text{hardness}| \times 100$ | 5.7 | 5.3 | 5.4 | 5.4 | 5.2 | 5.4 |

TABLE 6

| | | Rubber composition No. | 47 | 48 | 49 | 50 | 51 | 52 |
|---|---|---|---|---|---|---|---|---|
| Formulation (parts by mass) | (a) | BR730 | 100 | 100 | 100 | 100 | 100 | 100 |
| | | ZNDA90S | 19.65 | 19.65 | 29.55 | 29.55 | 39.4 | 39.4 |
| | (d) | Zinc oxide | 5 | 5 | 5 | 5 | 5 | 5 |
| | (c) | Dicumyl peroxide | 0.8 | 0.8 | 0.8 | 0.8 | 0.8 | 0.8 |
| Crosslinking component | | Acrylate (parts by mass) | 12.1 | 12.1 | 18.2 | 18.2 | 24.3 | 24.3 |
| | | Zinc (parts by mass) | 9.6 | 9.6 | 12.4 | 12.4 | 15.2 | 15.2 |
| Evaluation | Molding conditions | Temperature (° C.) | 150 | 170 | 150 | 170 | 150 | 170 |
| | | Time (min) | 20 | 20 | 20 | 20 | 20 | 20 |
| | Slab properties | Shore C hardness | 58.9 | 82.6 | 75.5 | 79.2 | 85.0 | 89.1 |
| | | Lupke type rebound resilience (%) | 69.5 | 67.2 | 65.4 | 63.8 | 61.7 | 60.0 |
| | | Storage modulus E' ($\times 10^7$ Pa) | 3.3 | 4.4 | 11.5 | 14.3 | 16.9 | 16.5 |
| | | Loss modulus E'' ($\times 10^7$ Pa) | 0.058 | 0.093 | 0.20 | 0.25 | 0.36 | 0.52 |

TABLE 6-continued

| Rubber composition No. | 47 | 48 | 49 | 50 | 51 | 52 |
|---|---|---|---|---|---|---|
| \|log(E'/E''$^2$)\| | 4.0 | 4.3 | 4.6 | 4.6 | 4.9 | 5.2 |
| \|log(E'/E''$^2$)\|/hardness\| × 100 | 6.8 | 6.9 | 6.0 | 5.8 | 5.8 | 5.9 |

The materials used in Tables 1-6 are shown as follows.

BR730: high-cis polybutadiene (amount of cis-1,4 bond=96 mass %, amount of 1,2-vinyl bond=1.3 mass %, Moony viscosity (ML$_{1+4}$ (100° C.)=55, molecular weight distribution (Mw/Mn)=3) available from JSR Corporation ZN-DA90S: zinc acrylate (a product coated with zinc stearate in an amount of 10 mass %) available from Nisshoku Techno Fine Chemical Co., Ltd.

Zinc oxide: "Ginrei R" available from Toho Zinc Co., Ltd.

Figure 5:
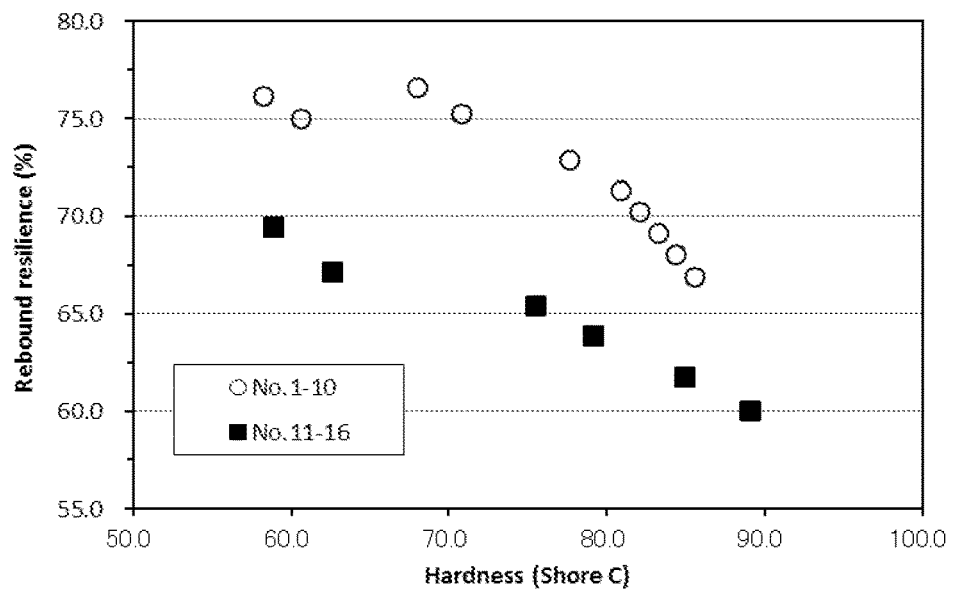
FIG. 5 shows a relationship between a slab hardness and a rebound resilience of a crosslinked rubber molded product.

Dicumyl peroxide: "Percumyl (register trademark) D" available from NOF Corporation Tables 1, 2 show the hardness and rebound resilience of the slab formed from each rubber composition. In addition, Tables 1, 2 show the amount of the crosslinking component (the acrylate group in (b) the co-crosslinking agent, and the metal in (b) the co-crosslinking agent and (d) the metal compound) contained in each rubber composition. FIG. 5 shows a relationship between the slab hardness and the rebound resilience of the crosslinked rubber molded product. The rubber compositions No. 1 to 10 are the cases in which (b) the co-crosslinking agent contains the complex represented by the general formula (1). The crosslinked rubber molded products (slabs) formed from these rubber compositions each have high resilience performance.

Figure 6:
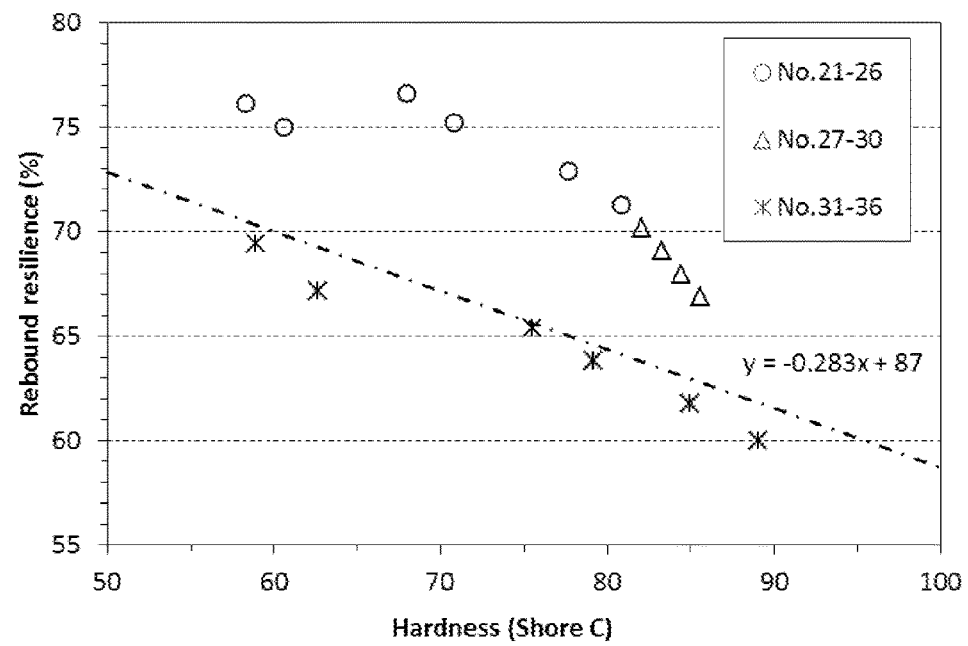
FIG. 6 shows a relationship between a slab hardness and a rebound resilience of a crosslinked rubber molded product.

Tables 3, 4 show the slab hardness and rebound resilience of the crosslinked rubber molded product formed from each rubber composition. In addition, Tables 3, 4 show the amount of the crosslinking component (the acrylate group in (b) the co-crosslinking agent, and the metal in (b) the co-crosslinking agent and (d) the metal compound) contained in each rubber composition. Further, FIG. 6 shows a relationship between the slab hardness and the rebound resilience of the crosslinked rubber molded product. The rubber compositions No. 21 to 30 are the cases in which (b) the co-crosslinking agent contains the complex represented by the formula (1), and the slab hardness (Shore C) X and the Lupke type rebound resilience (%) Y of the crosslinked rubber molded product satisfy the relationship of Y≥87−0.283X, The crosslinked rubber molded products formed from these rubber compositions also have excellent resilience performance.

Figure 7:
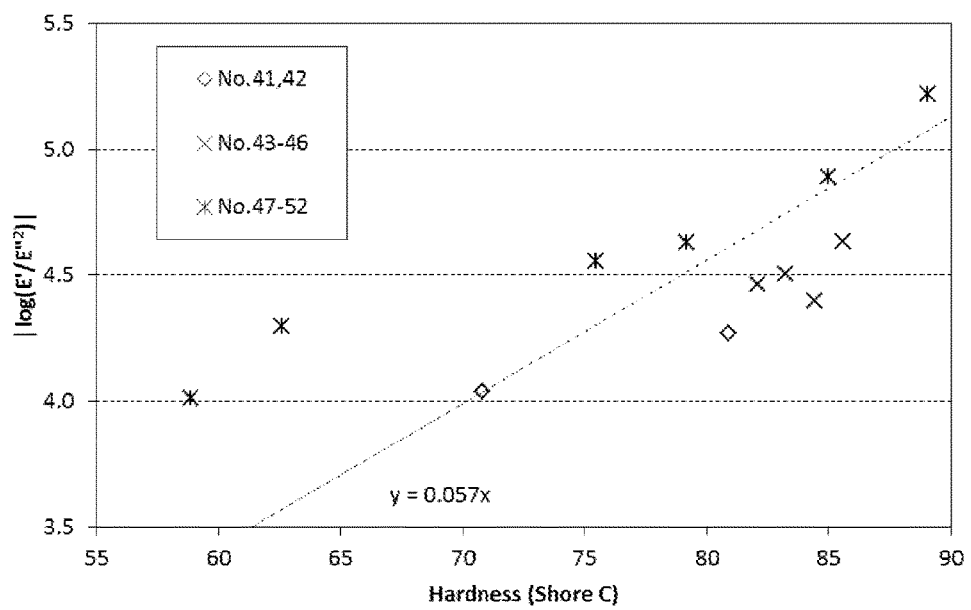
FIG. 7 shows a relationship between a slab hardness and |log(E'/E"$^2$)| of a crosslinked rubber molded product.

Tables 5, 6 show the slab hardness, storage modulus and loss modulus of the crosslinked rubber molded product formed from each rubber composition. In addition, Tables 5, 6 show the amount of the crosslinking component (the acrylate group in (b) the co-crosslinking agent, and the metal in (b) the co-crosslinking agent and (d) the metal compound) contained in each rubber composition. Further, FIG. 7 shows a relationship between the slab hardness and \|log(E'/E''$^2$)\| of the crosslinked rubber molded product. The rubber compositions No. 41 to 46 are the cases in which (b) the co-crosslinking agent contains the complex represented by the formula (1), and the storage modulus E' (Pa) and loss modulus E'' (Pa) and the slab hardness (Shore C) X of the crosslinked rubber molded product satisfy the relationship of \|log(E'/E''$^2$)\|/X×100≤5.7. The crosslinked rubber molded products formed from these rubber compositions also have excellent resilience performance.

If the rubber composition according to the present invention is used, a crosslinked rubber molded product excellent in the resilience performance can be obtained. Thus, the rubber composition according to the present invention can be utilized in sports goods such as golf ball, tennis ball and grip, industrial products such as hose, belt and mat, shoe sole, tire, resin additive, antivibration rubber, fender, and so on.

This application is based on Japanese Patent Applications No. 2016-250053, No. 2016-250055, No. 2016-250056 filed on Dec. 22, 2016, and No. 2017-129266, No. 2017-129267 filed on Jun. 30, 2017, the contents of which are hereby incorporated by reference.

The invention claimed is:

1. A rubber composition containing (a) a base rubber, (b) a co-crosslinking agent and (c) a crosslinking initiator, wherein (b) the co-crosslinking agent contains a complex represented by a general formula (1):

(1)

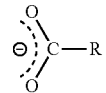
(2)

in the formula (1), M is a metal atom, and L is a carboxylate represented by a general formula (2); in the formula (2), R is a hydrogen atom, an alkyl group having 1 to 18 carbon atoms, an alkenyl group having 2 to 18 carbon atoms or an alkynyl group having 2 to 18 carbon atoms, and the dotted line shows a resonance structure; and in the formula (1), a plurality of R may be identical to or different from each other, and at least one of R is the alkenyl group having 2 to 18 carbon atoms or the alkynyl group having 2 to 18 carbon atoms.

2. The rubber composition according to claim 1, wherein (b) the co-crosslinking agent contains the complex represented by the general formula (1) in an amount of 5 mass % or more.

3. The rubber composition according to claim 1, wherein in the general formula (1), at least one of R is an alkenyl group having 2 to 8 carbon atoms and a carbon-carbon double bond at a terminal thereof, or an alkynyl group having 2 to 8 carbon atoms and a carbon-carbon triple bond at a terminal thereof.

4. The rubber composition according to claim 1, wherein in the general formula (1), at least two of R are an alkenyl group having 2 to 8 carbon atoms and a carbon-carbon double bond at a terminal thereof, or an alkynyl group having 2 to 8 carbon atoms and a carbon-carbon triple bond at a terminal thereof.

5. The rubber composition according to claim 1, wherein the complex represented by the general formula (1) is a complex represented by a structural formula (3):

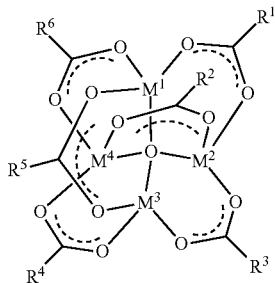

(3)

in the formula (3), $M^1$ to $M^4$ are identical to or different from each other and represent a metal atom, $R^1$ to $R^6$ are identical to or different from each other and represent a hydrogen atom, an alkyl group having 1 to 18 carbon atoms, an alkenyl group having 2 to 18 carbon atoms or an alkynyl group having 2 to 18 carbon atoms, and at least one of $R^1$ to $R^6$ is the alkenyl group having 2 to 18 carbon atoms or the alkynyl group having 2 to 18 carbon atoms.

6. The rubber composition according to claim 1, wherein (a) the base rubber contains a diene rubber or a natural rubber.

7. The rubber composition according to claim 1, wherein the rubber composition contains (b) the co-crosslinking agent in an amount ranging from 1 part by mass to 50 parts by mass with respect to 100 parts by mass of (a) the base rubber.

8. The rubber composition according to claim 1, wherein the metal atom of the complex represented by the general formula (1) has oxidation number of +2.

9. The rubber composition according to claim 1, wherein the rubber composition further contains (d) a metal compound.

10. The rubber composition according to claim 9, wherein (d) the metal compound is at least one metal oxide selected from the group consisting of calcium oxide, zinc oxide and magnesium oxide.

11. The rubber composition according to claim 9, wherein the rubber composition contains (d) the metal compound in an amount ranging from 0.5 part by mass to 20 parts by mass with respect to 100 parts by mass of (a) the base rubber.

12. The rubber composition according to claim 9, wherein (a) the base rubber contains a diene rubber or a natural rubber, (b) the co-crosslinking agent contains the complex represented by the general formula (1) in an amount of 5 mass % or more, and in the general formula (1), at least two of R are an alkenyl group having 2 to 8 carbon atoms and a carbon-carbon double bond at a terminal thereof, or an alkynyl group having 2 to 8 carbon atoms and a carbon-carbon triple bond at a terminal thereof.

13. A crosslinked rubber molded product formed from the rubber composition according to claim 12 and having a slab hardness in a range from 20 to 98 in Shore C hardness.

14. A crosslinked rubber molded product formed from the rubber composition according to claim 12 and having a Lupke type rebound resilience (JIS K6255) in a range from 55% to 98%.

15. A crosslinked rubber molded product formed from the rubber composition according to claim 12 and having a storage modulus E' (Pa) in a range from $3.0 \times 10^7$ Pa to $40 \times 10^7$ Pa, wherein the storage modulus E' (Pa) is measured with a dynamic viscoelasticity measuring apparatus under conditions of: tensile mode, measuring temperature of 24° C., oscillation frequency of 10 Hz and measuring strain of 0.05%.

16. A crosslinked rubber molded product formed from the rubber composition according to claim 12 and having a loss modulus E" (Pa) in a range from $0.001 \times 10^7$ Pa to $3.0 \times 10^7$ Pa, wherein the loss modulus E" (Pa) is measured with a dynamic viscoelasticity measuring apparatus under conditions of: tensile mode, measuring temperature of 24° C., oscillation frequency of 10 Hz and measuring strain of 0.05%.

17. A crosslinked rubber molded product formed from the rubber composition according to claim 12 and having a slab hardness (Shore C) X and a Lupke type rebound resilience (JIS K6255) (%) Y satisfying a relationship of $Y \geq 87 - 0.283X$.

18. A crosslinked rubber molded product formed from the rubber composition according to claim 12 and having a storage modulus E' (Pa), a loss modulus E" (Pa) and a slab hardness (Shore C) X satisfying a relationship of $|\log(E'/E''^2)|/X \times 100 \leq 5.7$, wherein the storage modulus E' (Pa) and the loss modulus E" (Pa) are measured with a dynamic viscoelasticity measuring apparatus under conditions of: tensile mode, measuring temperature of 24° C., oscillation frequency of 10 Hz and measuring strain of 0.05%.

19. A crosslinked rubber molded product formed from the rubber composition according to claim 1.

20. A golf ball comprising a constituent member formed from the rubber composition according to claim 1.

* * * * *